(12) United States Patent
Hinoki

(10) Patent No.: US 7,122,023 B1
(45) Date of Patent: Oct. 17, 2006

(54) ABSORBENT ARTICLE WITH ACQUISITION PORTION PROTRUDING THROUGH A TOPSHEET OPENING AND A STORAGE MEMBER OPENING

(75) Inventor: Nami Hinoki, Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/168,892

(22) PCT Filed: Dec. 22, 1999

(86) PCT No.: PCT/US99/30627

§ 371 (c)(1),
(2), (4) Date: Jun. 21, 2002

(87) PCT Pub. No.: WO01/45610

PCT Pub. Date: Jun. 20, 2001

(51) Int. Cl.
*A61F 13/537* (2006.01)
*A61F 13/512* (2006.01)
*A61F 13/472* (2006.01)

(52) U.S. Cl. .............. 604/385.101; 604/383; 604/378; 604/385.01

(58) Field of Classification Search ........... 604/385.01, 604/385.101, 385.12, 385.17, 378, 383, 385.09, 604/358; 128/118.1
See application file for complete search history.

(56) References Cited

U.S. PATENT DOCUMENTS

| | | | |
|---|---|---|---|
| 3,441,023 A | 4/1969 | Rijssenbeek | |
| 5,074,855 A * | 12/1991 | Rosenbluth et al. ... | 604/385.17 |
| 5,290,262 A * | 3/1994 | Vukos et al. .......... | 604/385.17 |
| 5,382,245 A * | 1/1995 | Thompson et al. ......... | 604/368 |
| 5,624,421 A * | 4/1997 | Dabi et al. ................... | 604/378 |
| 5,624,423 A * | 4/1997 | Anjur et al. ........... | 604/385.21 |
| 5,662,633 A * | 9/1997 | Doak et al. ................. | 604/378 |
| 5,743,896 A * | 4/1998 | Parker .................... | 604/385.01 |
| 5,947,945 A * | 9/1999 | Cree et al. ................... | 604/368 |

FOREIGN PATENT DOCUMENTS

| WO | WO 98/17217 A1 | 4/1998 |
|---|---|---|
| WO | WO 9817217 A1 * | 4/1998 |

\* cited by examiner

*Primary Examiner*—Tatyana Zalukaeva
*Assistant Examiner*—Laura C. Hill
(74) *Attorney, Agent, or Firm*—Gary J. Foose; Kevin C. Johnson; David M. Weirich

(57) ABSTRACT

An improved absorbent article is disclosed. The absorbent article has a longitudinal centerline and a lateral centerline, and comprises a topsheet, a backsheet, and an absorbent component. The topsheet has a topsheet opening. The absorbent component comprises a storage member and a distribution member. The storage member has a storage member opening surrounded by a periphery edge. The distribution member comprises an acquisition portion and a main portion wherein. The main portion extends underneath the storage member. The acquisition portion protrudes through the topsheet opening and the storage member opening, and extends over the topsheet longitudinally outwardly or laterally outwardly beyond the periphery edge of the storage member opening.

9 Claims, 13 Drawing Sheets

_US 7,122,023 B1_

ABSORBENT ARTICLE WITH ACQUISITION PORTION PROTRUDING THROUGH A TOPSHEET OPENING AND A STORAGE MEMBER OPENING

FIELD OF THE INVENTION

The present invention relates to absorbent articles such as sanitary napkins, panty liners, incontinence pads, and the like.

BACKGROUND

Absorbent articles such as sanitary napkins, panty liners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineum. Sanitary napkins of a wide variety of shapes and dimensions are currently used by women for the collection of menses and other bodily discharges.

In the past, a number of efforts have been directed at providing sanitary napkins that maintain contact with the wearer's body. One attempt to provide such body contact is disclosed in U.S. Pat. No. 2,747,575 issued May 29, 1956 to Mercer. The Mercer patent discloses a catamenial bandage having a longitudinal hump which bulges towards and may contact the body of the wearer.

U.S. Pat. No. 4,425,130 issued to DesMarais on Jan. 10, 1984, discloses a compound sanitary napkin that comprises a primary menstrual pad and a panty protector joined to one another at their corresponding ends in such a manner that the two constituents are free to move relative to one another along essentially their entire common length. The primary menstrual pad is intended to absorb the bulk of the bodily fluids discharged by the user, while the panty protector is intended to protect the user's garments from soiling. In use, the relative freedom of movement between the primary menstrual pad and the panty protector serves to maintain the primary menstrual pad adjacent to the user's crotch region while the panty protector remains associated with the user's undergarment.

PCT International Patent Application Publication No. WO 94/16658, entitled "Generally Thin, Flexible Sanitary Napkin With Central Absorbent Hump", published in the name of Osborn on Aug. 4, 1994, discloses a generally thin, flexible sanitary napkin which has a central absorbent hump, and is capable of handling medium to high menstrual flows.

Thus, the absorbent articles having humps are useful to allow close contact of the absorbent articles to the wearer's body, whereby the humps preferentially acquires body fluid. However, due to the limited size of the humps, such humps do not typically have sufficient absorption capacity for retaining the acquired body fluid over the period of the use of the absorbent article. Therefore, after the absorption capacity of the hump is exhausted by body fluid discharged from the wearer's body, body fluid tends to overflow from the hump and causes rewet feeling to the wearer and/or leakage from the absorbent article, thereby causing soil of the wearer's undergarment.

Thus, there is a need for an absorbent article which relatively quickly acquires body fluid discharged from the wearer's body. There is also a need for an absorbent article which relatively quickly moves absorbed body fluid away from the wearer's body. There is also a need for an absorbent article which relatively quickly moves absorbed body fluid into the absorbent article. There is also a need for an absorbent article which has an enhanced absorption capacity for body fluid.

SUMMARY

The present invention relates to an absorbent article such as sanitary napkins, panty liners, incontinence pads, and the like. The absorbent article has a longitudinal centerline and a lateral centerline, and comprises a topsheet, a backsheet, and an absorbent component. The topsheet has a topsheet opening. The absorbent component comprises a storage member and a distribution member. The storage member has a storage member opening surrounded by a periphery edge. The distribution member comprises an acquisition portion and a main portion wherein. The main portion extends underneath the storage member. The acquisition portion protrudes through the topsheet opening and the storage member opening, and extends over the topsheet longitudinally outwardly or laterally outwardly beyond the periphery edge of the storage member opening.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
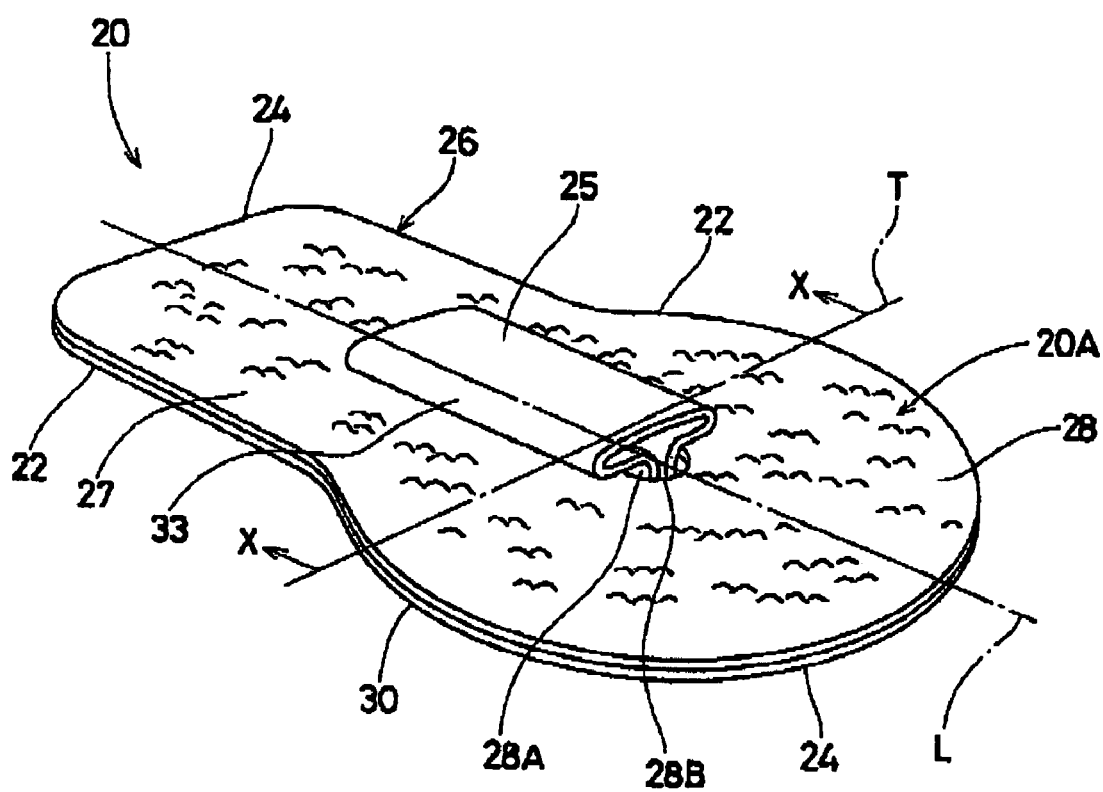
FIG. 1 is a perspective view of one embodiment of an absorbent article of the present invention.

All cited references are incorporated herein by reference in their entireties. Citation of any reference is not an admission regarding any determination as to its availability as prior art to the claimed invention.

"Comprising" means that other steps and other elements which do not affect the end result can be added. This term encompasses the terms "consisting of" and "consisting essentially of".

1. The Absorbent Article

The term "absorbent article", as used herein, refers to articles which absorb and contain body exudates, such as body fluid. More specifically, the term refers to articles which are placed against or in proximity to the body of the wearer to absorb and contain the various exudates discharged from the body. The term "absorbent article" is intended to include sanitary napkins, pantiliners, and incontinence pads (and other articles worn in the crotch region of a garment).

The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiments illustrated in FIGS. 1–5, the absorbent article is a menstrual pad designated 20 that is designed to replace conventional sanitary napkins.

The term "sanitary napkin", as used herein, refers to an article which is worn by females adjacent to the pudendal region that is intended to absorb and contain the various exudates which are discharged from the body (e.g., blood, menses, and urine). Although the present invention is shown in the drawings as a menstrual pad that is intended to replace conventional sanitary napkins. It should be understood that the present invention is not limited to the particular types or configurations of absorbent articles shown in the drawings.

Figure 2:
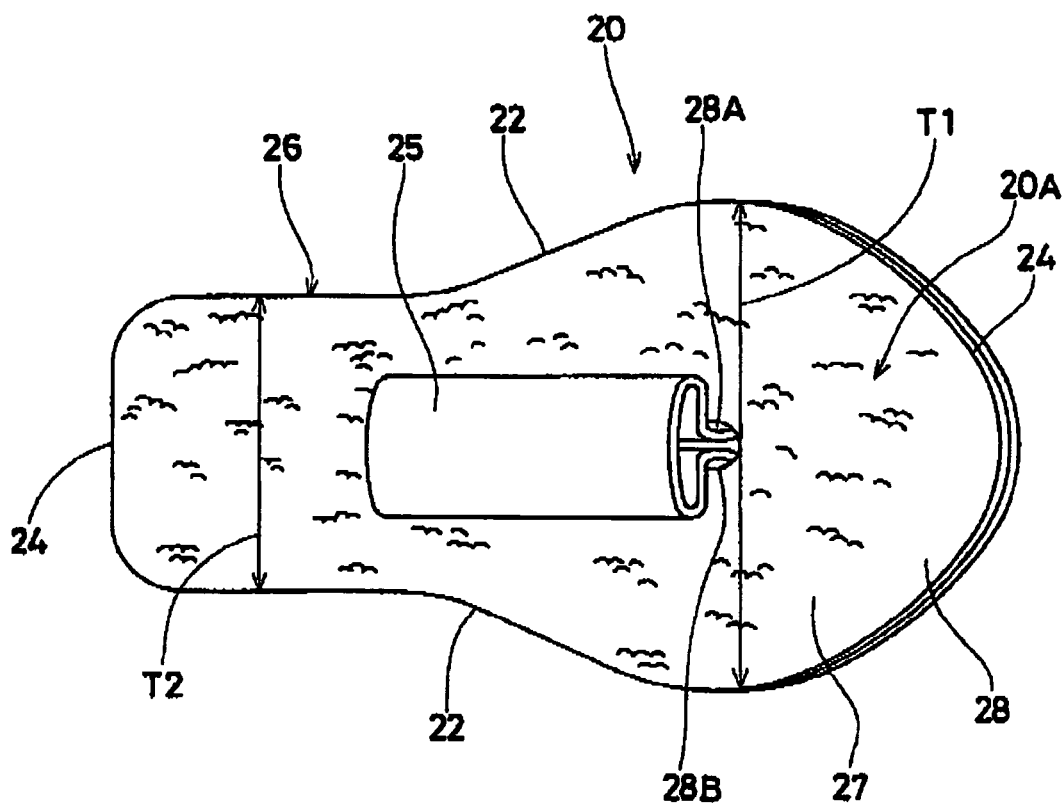
FIG. 2 is a top view of the absorbent article shown in FIG. 1.

The absorbent article 20 of the present invention has two sides or two surfaces, a body facing side or body facing surface 20A and a garment facing side or garment facing surface 20B. The absorbent article 20 is shown in FIGS. 1 and 2 as generally viewed from its body facing side 20A. The body facing side 20A is intended to be worn adjacent to the wearer's body. The garment facing side 20B (refer to FIG. 4) is intended to be placed adjacent to the supporting garment when the absorbent article 20 is worn.

The absorbent article 20 has two centerlines, a longitudinal centerline L and a transverse (or lateral) centerline T. The term "longitudinal", as used herein, refers to a line, axis or direction in the plane of the absorbent article 20 that is generally aligned with (e.g., approximately parallel to) a vertical plane which bisects a standing wearer into left and right body halves when the absorbent article 20 is worn. The terms "transverse" or "lateral" used herein, are interchangeable, and refer to a line, axis or direction which lies within the plane of the absorbent article 20 that is generally perpendicular to the longitudinal direction. The absorbent article also has two spaced apart longitudinal edges 22, two spaced apart transverse or end edges (or "ends") 24, which together form the periphery 26 of the absorbent article. In the embodiment shown in FIG. 1, the absorbent article 20 has a flat configuration.

The absorbent article 20 may have any suitable plan view configuration. Suitable configurations include, but are not limited to: oval; race-track shaped; shapes which have convexly-inward longitudinal side edges (e.g., hourglass shapes). In the particularly preferred embodiment shown in FIGS. 1–2, the absorbent article has a key-hole shape which has a wider rounded or oval portion which is preferably worn toward the rear of the wearer's body, preferably for covering at least a portion of the wearer's perineum and a generally rectangular extension therefrom (preferably with rounded edges) which is preferably worn toward the front of the wearer's body for covering at least a portion of the wearer's pudendal region.

The absorbent article may have an overall length of less than or equal to about 280 mm, preferably less than or equal to about 220 mm, more preferably less than or equal to about 160 mm, and of more than or equal to about 80 mm, preferably more than or equal to about 100 mm, more preferably more than or equal to about 120 mm. The absorbent article (without including the dimension of flaps or wings if any) may also have a width of less than or equal to about 160 mm, preferably less than or equal to about 140 mm, more preferably less than or equal to about 120 mm, and of more than or equal to about 40 mm, preferably more than or equal to about 50 mm, more preferably more than or equal to about 60 mm. In the preferred embodiment shown in FIG. 2, the absorbent article 20 may have a width T1 at the wider rounded portion of between about 80 mm and about 140 mm and a width T2 at the rectangular extension of between about 50 mm and about 80 mm.

The absorbent article 20 preferably acquires greater than or equal to 50%, preferably greater than or equal to 60%, more preferably greater than or equal to 70% of body fluid absorbed by the absorbent article 20, through the acquisition portion 25. Preferably, the absorbent article 20 acquires all the body fluid through the acquisition portion 25 when the absorbent article 20 is placed in a right position with the wearer's body.

FIGS. 1–5 show the individual components of the absorbent article 20 of the present invention. This embodiment of the absorbent article 20 preferably comprises at least three primary components. These include a body facing topsheet 28, a garment facing backsheet 30, and an absorbent component 32 positioned between the topsheet 28 and the backsheet 30. The absorbent component 32 includes a storage member 31 and a distribution member 33. The body facing topsheet, the garment facing backsheet, and the absorbent component can comprise a number of suitable materials, provided that the absorbent article 20 has the overall characteristics described herein.

The topsheet 28 is disposed over the absorbent component 32. The topsheet 28 has a void area, such as a topsheet opening or a topsheet aperture, 28A, and a periphery portion 27. Further, the topsheet opening is surrounded by a periphery edge 28B.

The topsheet opening 28A is disposed generally at the longitudinal and transverse (or lateral) center of the topsheet 28. Suitable configurations of the topsheet opening 28A include, but are not limited to, oval shape, race-track shape, or circle shape. Alternatively, the configuration of the topsheet opening 28A may be rectangle shape, triangle shape, or polygon shape. In the preferred embodiment shown in FIG. 3, the topsheet opening 28A preferably has an oval shape. The topsheet opening 28A may also extend along the longitudinal centerline L between the opposite end edges 24. If the topsheet opening 28A has such a configuration, the periphery portion 27 may be formed by two strips of the topsheet disposed along the opposite longitudinal edges 22.

The periphery portion 27 is placed in a specified positional relationship with respect to the area in the absorbent article 20 where body fluid is not typically deposited and with respect to a portion of the wearer's body where body fluid is not discharged, when the absorbent article 20 is placed in a right place with the wearer's body. It is preferable that the periphery portion 27 of the absorbent article 20 covers at least a portion of the surface of the wearer's labia majora. More preferably, the periphery portion 27 covers all the surface of the wearer's labia majora. The periphery portion 27 may cover a portion of the surface of the wearer's body outside the labia minora. When the acquisition portion 25 covers only a portion of the surface of the wearer's labia minora, the periphery portion 27 may extend into a portion of the wearer's labia minora (though it is less preferable). It is believed that the wearer becomes more sensitive to feeling wetness as it goes outwardly from the surface of the wearer's labia minora toward the surface of the labia majora, and further toward the surface of the wearer's body outside the labia majora. Therefore, it is important to provide reduced rewet (i.e., to maintain dryness) at the periphery portion 27 because the periphery portion 27 contacts the surface of the wearer's labia majora which is more sensitive to feeling wetness.

Preferably, the periphery portion 27 does not directly contact a portion of the wearer's body where body fluid is discharged when the absorbent article 20 is placed in a right position with the wearer's body. Preferably, body fluid is not typically deposited on the periphery portion 27. This reduces the opportunity that body fluid is absorbed into the absorbent component 32 at the periphery portion 27. Therefore, the periphery portion 27 remains relatively visually clean and relatively dry. The dryness at the periphery portion helps to isolate body fluid absorbed in the absorbent component 32 from the wearer's skin over a long period of time. Visual cleanness at the periphery portion 27 gives the wearer a feeling of security against leakage of body fluid because the periphery portion 27 remains visually clean.

The periphery portion 27 is disposed to surround the topsheet opening 28A. The periphery portion 27 of the topsheet 28 may include at least a portion of the topsheet 28 other than the topsheet opening 28A. Preferably, the periphery portion 27 includes the entire portion of the topsheet 28 other than the topsheet opening 28A. The periphery portion 27 isolates the absorbent component 32 (i.e., the storage member 31) from the wearer's skin and is preferably able to prevent rewet. The periphery portion 27 is preferably soft and may be relatively lofty. A portion of or the entirety of the periphery portion 27 does not necessarily need to have a function to allow penetration of body fluid, i.e., the periphery portion 27 may be liquid impermeable to completely prevent rewet, because body fluid is not deposited at the periphery portion 27 when the absorbent article is placed in a right position with the wearer's body. However, body fluid may be accidentally deposited onto the periphery portion 27 by, e.g., misplacement of the absorbent article 20 with the wearer's body. Therefore, it is preferable that the periphery portion 27 is liquid permeable. The liquid permeable periphery portion 27 may have vapor permeability. The periphery portion 27 can be optimized to prevent rewet and/or to improve softness to the wearer's skin without a need to compromise with inconsistent functions, such as superior body fluid acquisition. In order to prevent rewet, the periphery portion 27 may have less hydrophilicity than the element of the absorbent component 32. Preferably, the periphery portion 27 has less hydrophilicity than the storage member 31 which is contiguous with the periphery portion 27. The periphery portion 27 may be even hydrophobic.

The topsheet 28 is preferably compliant, soft feeling, and non-irritating to the wearer's skin. A suitable topsheet 28 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 28 is preferably made of a hydrophobic material to isolate the wearer's skin from body fluids which have absorbed in the absorbent component 32 (i.e., to prevent rewet). However, in case body fluid discharged from the wearer is accidentally deposited on the topsheet 28, at least the upper surface of the topsheet 28 may be treated to be hydrophilic so that liquids will transfer through the topsheet more rapidly. This diminishes the likelihood that body fluid will flow off the topsheet 28 rather than being drawn through the topsheet 28 and being absorbed by the absorbent component 32. The topsheet 28 can be rendered hydrophilic by treating it with a surfactant. Suitable methods for treating the topsheet 28 with a surfactant include spraying the topsheet 28 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991. Alternatively, surfactant may be impregnated into the fibers or resin and the topsheet 28 may be formed by the fibers with impregnated surfactant.

In one preferred embodiment, the periphery portion 27 of the topsheet 28 may comprise an apertured formed film. Apertured formed films are preferred for the topsheet 28 because they are permeable to body fluid and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. One especially preferred material for the topsheet 28 comprises a formed film described in one or more of the above patents and marketed on sanitary napkins by The Procter & Gamble Company of Cincinnati, Ohio as the "DRI-WEAVE" topsheet. The periphery portion 27 may have a hydrophilic surfactant incorporated therein during manufacture if necessary.

Other preferred apertured films suitable for use as the periphery portion 27 of the topsheet 28 are the apertured films made in accordance with U.S. Pat. Nos. 4,609,518 and 4,629,643, the latter entitled "Microapertured Polymeric Web Exhibiting Soft and Silky Tactile Impression", both issued to Curro, et al., on Sep. 2, 1986, and Dec. 16, 1986, respectively, and cloth-like formed films made in accordance with U.S. Pat. No. 4,637,819 entitled "Macroscopically Expanded Three-Dimensional Polymeric Web for Transmitting Both Dynamically Deposited and Statically Contacted Fluids From One Surface to the Other", which issued to Ouellette, et al. on Jan. 20, 1987; and U.S. patent application Ser. No. 08/442,935 entitled "Fluid Transport Webs Exhibiting Surface Energy Gradients" filed in the name of Ouellette, et al. on May 31, 1995 (PCT Publication WO 96/00548, published Jan. 11, 1996).

If such an apertured film topsheet material is used, it can be used as the periphery portion 27 per se. Preferably, however, it is used in conjunction with nonwoven topsheet material wherein the nonwoven topsheet material overlies such an apertured film. The apertured film, if properly apertured, will provide a reduced tendency for liquids to pass back through and rewet the wearer's skin. Combining both the nonwoven topsheet material and the cloth-like apertured formed film spaces the absorbent component and liquids therein from the wearer's body, further contributing to keeping the wearer's body dry.

In another embodiment, the topsheet 28 may be formed by a high loft fibrous material. Herein, the term "high loft fibrous material" refers to a low density, but relatively high caliper, fibrous material. It is often assumed that leakage of menses from conventional sanitary napkins occurs primarily as a result of the capacity of absorbent articles being exceeded. However, it has been found that a substantial number of soiling accidents occur as a result of menstrual fluid that does not even enter the sanitary napkin. Often these soiling accidents result from menses which flows adjacent to the wearer's body, and which may flow in or close to the wearer's pubic hair. The absorbent article of the present invention tends to directly and rapidly acquire body fluid at the source of body fluid of the wearer's body, e.g., at the surface of the wearer's labia minora. Therefore, the risk of body fluid flowing adjacent to the wearer's body is reduced. However, it may accidentally happen when the wearer moves, such as walks. For this case, a topsheet with a high degree of "loft" is preferred so that the fibers of the topsheet will get into close contact with the wearer's body and between the wearer's pubic hairs. The high loft topsheet tends to break the flow of menses along the wearer's body, and intercepts menses flowing along the wearer's body, and allows such bodily exudates to be acquired into the absorbent core. Such high loft topsheets may provide a capillary structure that effectively competes with the wearer's body for bodily fluids, such as menses, and directs such fluids into the absorbent article. A good indicator of whether an absorbent article has a body-contacting surface with Z-direction oriented elements is whether the elements on the body-contacting surface are capable of penetrating between the wearer's pubic hairs. Conversely, if the elements comprising the body-contacting surface of the absorbent article lie flat against the wearer's pubic hairs, and compress the pubic hairs, this is an indication that the absorbent article does not have a body-contacting surface with Z-direction oriented elements. One of the preferred topsheet materials is obtained as product code #W-4635 from Stearns Technical Textile of Cincinnati, Ohio. Another preferred high loft topsheet material is obtained as product code r #68317 (rebulked) from Fibertex A/S, Box 8029, Svendborgvej 16, DK-9220 Aalborg Ost, Denmark.

In still other embodiments, the periphery portion 27 of the topsheet 28 may be formed by a thin plastic film being liquid impermeable. The plastic film may have a vapor permeability.

The absorbent component 32 comprises a storage member 31 and a distribution member 33. Further, the storage member 31 comprises a storage member opening 31A and a storage portion 31B. The distribution member 33 comprises an acquisition portion 25, a connecting portion 33A and a main portion 33B.

The acquisition portion 25 of the distribution member 33 which extends over the topsheet preferably contacts and covers at least a portion of the surface of the wearer's labia minora when the absorbent article 20 is applied on the wearer's body. It is known that body fluid eventually flows out from the wearer's body through the space between the interior surfaces of the wearer's labia minora. Therefore, the direct contact of the absorbent component with portions of the surfaces of the wearer's labia minora provides an opportunity for superior acquisition of body fluid at the source of body fluid. Further, because the absorbent component 32 typically has ability to acquire body fluid higher than an ordinary topsheet material, body fluid tends to enter the absorbent component rather than flowing on the surface of the absorbent component 32. This reduces body fluid flowing on the body facing side of the absorbent article 20, thereby reducing leakage of body fluid, compared with a conventional product having a topsheet on which body fluid sometimes flows and leaks.

The storage member 31 and the distribution member 33 have dimensions smaller than the topsheet 28 and the backsheet 30. In the preferred embodiment shown in FIGS. 3 and 4, the main portion 33B of the distribution member 33 is disposed at the garment facing side 20B, i.e., at the side of the backsheet 30 and disposed between the backsheet 30 and the storage member 31. The acquisition portion 25 of the distribution member 33 is disposed at the body facing side 20A. The acquisition portion 25 and the main portion 33B are connected by the connecting portion 33A such that body fluid can transfer from the acquisition portion 25 to the main portion 33B. The storage member 31 is disposed between the topsheet 28 and the main portion 33B of the distribution member 33. At least a portion of the storage member 31 and at least a portion of the distribution member 33 are disposed to contact one another to form a contact surface. Body fluid is able to transfer from the distribution member 33 to the storage member 31 through the contact surface. Preferably, the entire portion of the storage member 31 is disposed in contact with the distribution member 33. Accordingly, body fluid which is absorbed by the acquisition portion 25 is able to transfer from the acquisition portion 25 to the main portion 33B, and then from the main portion 33B to the storage member 31. The storage member 31 and the distribution member 33 are preferably joined to each other to maintain integrity of the absorbent component. They may be joined by a regular or irregular patterned layer of adhesive, or any array of separate lines, spirals, or spots of adhesive. Alternatively, they may be joined by any other methods, such as bonding by applying pressure. It should be understood that for purposes of this invention, these types of members are not necessarily limited to single layers or sheets of material. Thus, the storage member 31 and the distribution member 33 may actually comprise laminates or combinations of several sheets or webs of the requisite type of materials.

The storage member 31 has a void area, such as a storage member aperture or a storage member opening, 31A, and a storage portion 31B. Further, the storage member opening 31A is surrounded by a periphery edge 31E.

The storage member opening 31A is disposed generally at the longitudinal and transverse center of the storage member 31. Preferably, the storage member opening 31A is a little bigger than the topsheet opening 28A to secure no interference of body fluid flow by the storage portion 31B. Suitable configurations of the storage member 31A include, but are not limited to, oval shape, race-track shape, or circle shape. Alternatively, the configuration of the storage member opening 31A may be rectangle shape, triangle shape, or polygon shape. In the preferred embodiment shown in FIG. 3, the storage member opening 31A preferably has an oval shape and has the generally same shape as the topsheet opening 28A, though the size of the storage member opening 31A is a little bigger than the topsheet opening 28A. The storage member opening 31A may also extend along the longitudinal centerline L between the opposite end edges 24. If the storage member opening 31A has such a configuration, the storage member 31 may be formed by two strips disposed along the opposite longitudinal edges 22.

The storage member opening 31A serves as a gateway in cooperation with the topsheet opening 28A of the topsheet 28 for fluid to be acquired into the distribution member 33.

The storage portion 31B of the storage member 31 is disposed to surround the storage member opening 31A. The storage portion 31B includes at least a portion of the storage member 31 other than the storage member opening 31A. Preferably, the storage portion 31B includes the entire portion of the storage member 31. The storage portion 31B has a top surface 31C and the bottom surface 31D. The top surface 31C is disposed at the side of the topsheet 28 and the bottom surface 31D is disposed at the side of the distribution member 33. Body fluid is first absorbed by the acquisition portion 25 of the distribution member 33 and is distributed to the main portion 33B and the storage portion 31B has less tendency to be expected to gush of body fluid. The storage portion 31B serves to absorb body fluid distributed to the storage portion 31B by the distribution member 33 and/or body fluid overflowed from the distribution member 33. Thus, the storage portion 31B draws body fluid away from the distribution member 33 such that preferably much of capacity of the distribution member 33 becomes available again for another gush of body fluid. In addition, because body fluid is absorbed from the bottom surface 31D which contacts with the distribution member 33, the capacity of the storage portion 31B is exhausted from the bottom surface 31D toward the top surface 31C. This allows the top surface 31C of the storage portion 31B to remain relatively visually clean and dry. In order to sustain these benefits as long as possible over a period of use of the absorbent article 20, the storage portion 31B should not absorb body fluid too rapidly and have sufficient capacity. It is preferable to control the absorption of the storage portion 31B such that body fluid does not reach the top surface 31C over a period of use of the absorbent article. The dryness at the top surface of the storage portion 31B serves to isolate body fluid from the wearer's and to prevent body fluid from passing out of the absorbent component 32 back through the topsheet 28 and onto the skin of the wearer. The storage portion 31B also helps to provide visually clean impression at the body facing side 20A of the absorbent article 20. Although it is preferable that body fluid is not deposited onto the periphery portion 27 when the absorbent article is placed in a right position with the wearer's body, the storage member 31 may collect body fluid deposited onto the storage member 31 through the periphery portion 27 of the topsheet 28.

The storage portion 31B has sufficient capacity to draw body fluid from the distribution member 33. Preferably, the storage portion 31B has capacity greater than or equal to the amount of body fluid discharged from the wearer over a period of use of the absorbent article. The storage portion 31B preferably has capacity greater than or equal to about 10 grams, more preferably greater than or equal to about 20 grams, or greater than or equal to about 25 grams. In order to impart high capacity to the storage portion 31B, the storage portion 31B may include highly absorbent material such as superabsorbent hydrogel-forming polymeric material. The storage portion 31B preferably may have the generally same capillarity as the distribution member 33. Preferably, the storage portion 31B may have a little greater capillarity than the distribution member 33. It helps to establish a positive capillarity force gradient from the distribution member 33 to the storage portion 31B. The positive capillarity force enables a positive liquid transfer force from the distribution member 33 to the storage portion 31B. While liquid capillarity can be defined in several ways (e.g., pore size, density, basis weight, etc.), the density and basis weight of the structure are the preferred parameters to define liquid capillarity.

The storage portion 31B has a density and a basis weight per unit area. The density and basis weight values of the storage portion 31B include the weight of the particles of hydrogel-forming material, such that the density and basis weight values will vary depending upon the amount of particles dispersed throughout the storage portion 31B. Thus, the storage portion 31B will generally have a density of from about 0.03 to about 0.3 g/cm3, and more preferably within the range of from about 0.05 to about 0.2 g/cm3, wherein the storage member contains up to about 60% by weight of particles of absorbent gelling material. The basis weight of such a storage portion 31B can range from about 0.01 to about 0.1 g/cm2, preferably from about 0.015 to about 0.03 g/cm2. The density of the holding zone is calculated from its basis weight and caliper measured on newly unpacked, unfolded, and dissected absorbent article. The caliper is measured using a standard gauge with a sample under a load of 0.1 psi. The basis weight is measured by die-cutting a certain size sample and weighing this sample on a standard scale, the weight and area of the sample determining the basis weight. (It should be noted that the density and basis weight values include the weight of the particles of hydrogel-forming material).

Various types of hydrophilic material can be used in the storage member 31. Any type of hydrophilic fibers which are suitable for use in conventional absorbent products are also suitable for use in the storage member 31. Examples of suitable absorbent materials include comminuted wood pulp which is generally referred to as airfelt; creped cellulose wadding; meltblown polymers including coform; chemically stiffened, modified or cross-linked cellulosic fibers, synthetic fibers such as crimped polyester fibers; peat moss; tissue including tissue wraps and tissue laminates; absorbent foams; absorbent sponges; superabsorbent hydrogel-forming polymeric material; absorbent gelling materials; or any equivalent material or combinations of materials, or mixtures of these. The configuration and construction of the absorbent component may also be varied (e.g., the absorbent component may have varying caliper zones (e.g., profiled so as to be thicker in the center), hydrophilic gradients, superabsorbent gradients, or may comprise one or more layers or structures.

In one embodiment, the storage member 31 comprises an airlaid web with particulate or fibrous superabsorbent hydrogel-forming polymeric material dispersed therein. The airlaid web can comprise a number of different types of materials. In one version of this embodiment, the absorbent component may comprise a blend of synthetic polymeric fibers, cellulosic fibers, and particulate or fibrous superabsorbent hydrogel-forming polymeric material. In another version of this embodiment, the storage portion 31B may comprise only synthetic polymeric fibers and fibrous or particulate superabsorbent hydrogel-forming polymeric material. In still another version of this embodiment, the storage member 31 may be comprised entirely of cellulosic fibers (such as airfelt) and particulate or fibrous superabsorbent hydrogel-forming polymeric material. However, it is preferred that the storage member 31 comprises at least some synthetic material to increase its compression resistance and resiliency.

A suitable fibrous superabsorbent, hydrogel-forming polymeric material is sold as FIBERDRI superabsorbent by Camelot Technologies Ltd. of High River, Canada. The FIBERDRI fibrous superabsorbent material is preferred because it has more capacity than many current particulate superabsorbent materials. For example, it may have a capacity of about 25 grams of liquid per gram of superabsorbent material, whereas current particulate superabsorbent materials may have a capacity of about 20 grams/gram. The FIBERDRI material, thus, provides the advantage that a relatively small amount (for example, about 0.7 grams) of the FIBERDRI material will provide a total amount of capacity for the small sized absorbent component used in the present invention, which is equal to or greater than the total amount of capacity of full-sized sanitary napkins.

In another embodiment, the storage member 31 can comprise a laminate of tissue and superabsorbent hydrogel-forming polymeric material. Absorbent cores comprising laminates of tissue and superabsorbent hydrogel-forming polymeric material which can be modified for use herein are described generally in U.S. Pat. Nos. 4,950,264 and 5,009,653, both issued to Osborn.

In another embodiment, the storage member 31 may comprise a needle punched airlaid nonwoven web. In a preferred version of such an embodiment, the needle punched airlaid nonwoven web comprises about 40% by weight of fibrous superabsorbent hydrogel-forming polymeric material and about 60% polyester fibers. (Unless otherwise stated, all percentages specified herein are based upon weight.)

In a particularly preferred embodiment, the storage member 31 comprises a needle punched nonwoven material comprising rayon fibers and fibrous superabsorbent hydrogel-forming polymeric material. Such a nonwoven material preferably comprises between about 50% to about 70% preferably about 65% staple length viscose rayon fibers, and between about 30% and about 50%, preferably about 35% fibrous superabsorbent hydrogel-forming polymeric material. Suitable viscose rayon fibers are LYOCELL viscose rayon fibers, type 18453, obtained from Courtaulds Fibers, Inc. of North Axis, Alabama. Suitable fibrous superabsorbent hydrogel-forming polymeric material is the FIBERDRI fibrous superabsorbent material discussed above. The needle punched nonwoven material preferably has a basis weight of about 0.02 g/cm$^2$. This nonwoven material is preferably needle punched with about 60 needles/cm$^2$, or more. The more needles used, the higher will be the flexibility of the finished material. Although a single layer of this material can be used for the storage member 31, at least two members may be used. More than two members can be used, particularly if the material is made in lower basis weights. The members may be joined together, if desired. However, it has been found that the members are adequately retained in position relative to each other when they are simply placed adjacent to each other. This is believed to be due to the fiber entanglement between the fibers on the surfaces of the layers.

In another embodiment, the storage member 31 may comprise a carded, thermally-bonded airlaid nonwoven web. An example of such a material comprises about 20% FIBERDRI superabsorbent material fibers, about 25% bicomponent fibers, and about 55% cellulose fluff, and has a basis weight of about 0.08 g/cm$^2$.

Figure 3:
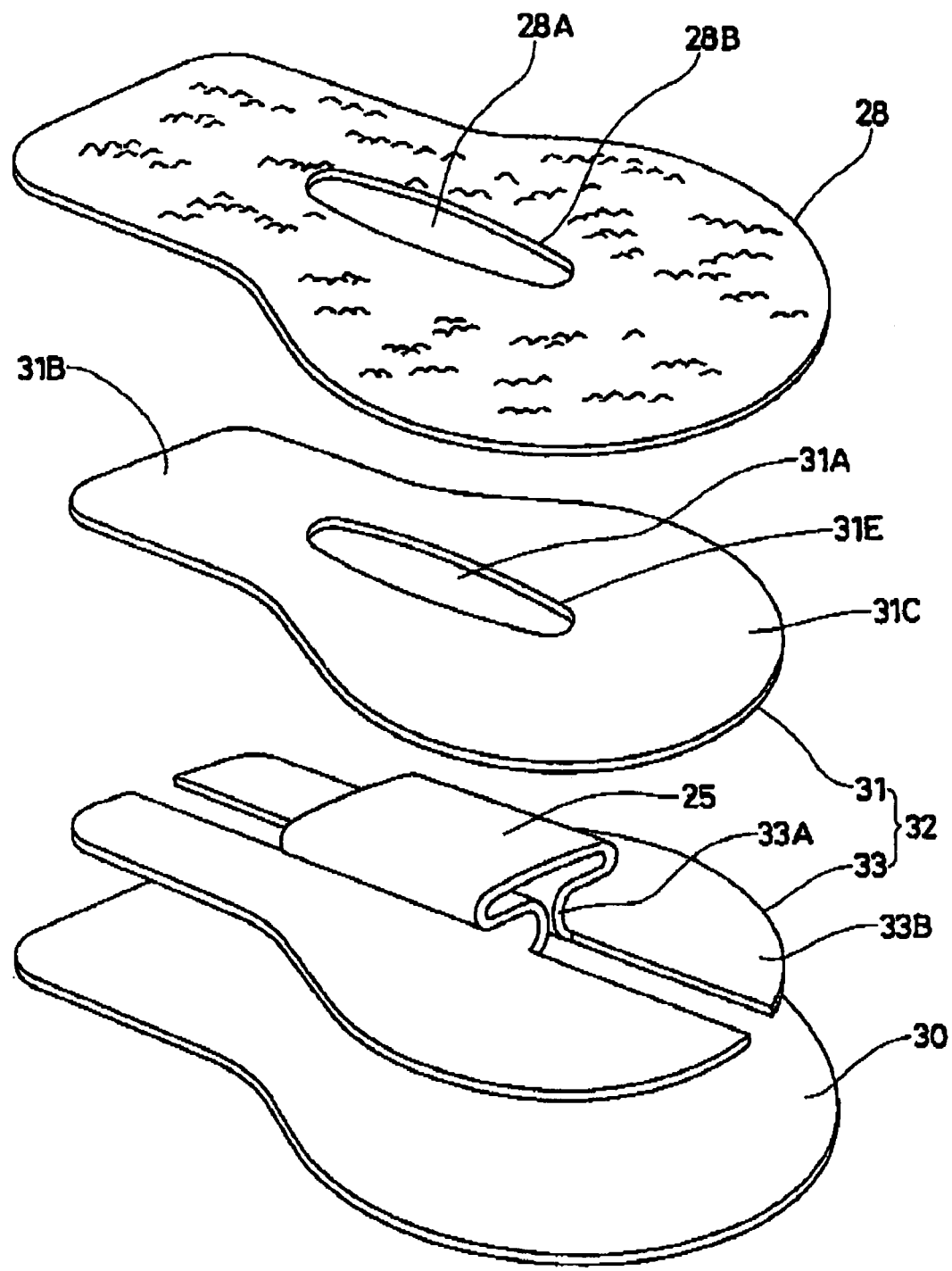
FIG. 3 is an exploded perspective view of the absorbent article shown in FIG. 1.

The distribution member 33 comprises an acquisition portion 25, a connecting portion 33A and a main portion 33B (refer to FIG. 3). The acquisition portion 25 of the distribution member 33 is disposed at the body facing side 20A. The main portion 33B of the distribution member 33 is disposed underneath the storage member 31. The acquisition portion 25 and the main portion 33B are connected by the connecting portion 33A such that body fluid can transfer from the acquisition portion 25 to the main portion 33B. Preferably, the acquisition portion 25 and the main portion 33B are formed by a single material. Alternatively, they may be formed by a plurality of materials which are joined each other. In this case, the acquisition portion 25 and the main portion 33B should be connected by the connecting portion 33A such that body fluid can transfer from the acquisition portion 25 to the main portion 33B. By this structure, it is possible that body fluid is quickly transferred from the acquisition portion 25 to the main portion 33B.

The acquisition portion 25 of the distribution member 33 protrudes through the storage member opening 31A and the topsheet opening 28A. Further, the acquisition portion 25 of the distribution member 33 extends over the topsheet 28 longitudinally outwardly or laterally outwardly beyond the periphery edge 31E of the storage member opening 31A, therefore is able to directly cover and contact a portion of the surface of the wearer's labia minora through the storage member opening 31A and the topsheet opening 28A. The term "longitudinally outwardly beyond the periphery edge", as used herein, refers to the direction from "the periphery edge" toward "the end edges 24" in the horizontal plane of the absorbent article 20. The term "laterally outwardly beyond the periphery edge", as used herein, refers to the direction from "the periphery edge" toward "the longitudinal edges 22" in the horizontal plane of the absorbent article 20. The acquisition portion 25 of the distribution member 33 may extend over the topsheet 28 at least longitudinally outwardly or laterally outwardly beyond the periphery edge 31E of the storage member opening 31A. In the embodiments of FIG. 1 of the present invention, the acquisition portion 25 of the distribution member 33 extends laterally outwardly beyond the periphery edge 31E. Alternatively, the acquisition portion 25 of the distribution member 33 extends over the topsheet 28 both longitudinally outwardly and laterally outwardly beyond the periphery edge 31E of the storage member opening 31A.

The distribution member 33 also contacts at least a portion of the storage member 31, therefore is able to transfer body fluid acquired in the distribution member 33 to the storage member 31. Preferably, the distribution member 33 is disposed underneath the entire area of the storage member opening 31A and the entire area of the storage portion 31B. Alternatively, the distribution member 33 may be disposed underneath only a portion of the storage member opening 31A.

The distribution member 33 serves to rapidly collect and transport discharged body fluid into and throughout itself. Since such body fluid is often discharged in gushes, the distribution member 33 must have some gush handling capacity so as to allow body fluid to freely and quickly move into the distribution member 33 and the ability to transport liquids from the point of initial contact on the distribution member 33 to other parts of the distribution member 33. The distribution member 33 also may provide a member that contains and quickly acquires subsequent gushes of liquid.

The distribution member 33 must have some gush handling capacity so that the distribution member 33 can rapidly receive practical quantities of body fluid. The gush handling capacity of the distribution member 33 is related to the void volume of the structure of the distribution member 33. The distribution member 33 should, therefore, be manufactured of a material that has sufficient void volume in the interstices or capillaries between the material or fibers to contain practical quantities of body fluid. Void volume within the distribution member 33 serves as a reservoir or "bucket" for large gushes of body fluid with a minimum resistance to flow within the structure so that the distribution member 33 may acquire and transport rapidly voided body fluid.

It has been found that the distribution member 33 should have a percentage void volume greater than or equal to about 80%, preferably greater than or equal to about 90%, more preferably greater than or equal to about 95% (typically between about 93% and 99%), so that there is sufficient void volume to contain in-use quantities of liquids or body exudates. The percentage void volume is calculated by the equation:

Percentage void volume=$(1-Vm/Vs) \times 100\%$ wherein Vm is the volume of the material determined by dividing the weight of the material or fibers in a given sample by the density of the material or fibers, and wherein Vs is the volume of the sample calculated by multiplying its area times its caliper measured under a load of 0.1 psi. Preferably, the distribution member 33 has a void volume of at least about 5 $cm^3$, more preferably at least about 10 $cm^3$, and most preferably at least about 15 $cm^3$. In an especially preferred embodiment, the distribution member has a void volume of about 20 $cm^3$.

In order to maintain a high void volume and a high level of liquid transport, it is believed that the distribution member 33 should have caliper, measured under a load of 0.1 psi, of greater than or equal to about 0.5 mm, preferably greater than or equal to about 1.0 mm, more preferably greater than or equal to about 1.5 mm, and further more preferably greater than or equal to about 2.0 mm. The basis weight of the distribution member 33 is preferably between about 0.005 to about 0.04 $g/cm^2$, more preferably about 0.015 $g/cm^2$ to about 0.025 $g/cm^2$.

Various types of hydrophilic material can be used in the distribution member 33 of the absorbent component 32. Any type of hydrophilic fibers which are suitable for use in conventional absorbent products are also suitable for use in the distribution member 33. Examples of suitable absorbent materials include comminuted wood pulp which is generally referred to as airfelt; creped cellulose wadding; meltblown polymers including coform; chemically stiffened, modified or cross-linked cellulosic fibers, synthetic fibers such as crimped polyester fibers; high surface area fibers; peat moss; tissue including tissue wraps and tissue laminates; absorbent foams; absorbent sponges; superabsorbent polymers; absorbent gelling materials; or any equivalent material of combinations of materials, or mixtures of these.

In one embodiment, the distribution member 33 may be formed by chemically stiffened, twisted, and curled bulking fibers; high surface area fibers; and binder fibers. The distribution member comprising these elements is described generally in U.S. Pat. No. 5,549,589 issued to Horney et al. on Aug. 27, 1996.

In a particularly preferred embodiment, the distribution member 33 comprises a nonwoven material comprising rayon fibers such as viscose rayon fibers and high surface area fibers such as eucalyptus fibers. Such high surface area fibers are useful to increase body fluid distribution in the distribution member 33. Such a nonwoven material preferably comprises between about 50% to about 70%, preferably about 65% staple length viscose rayon fibers, and between about 30% and about 50%, preferably about 35% of eucalyptus fibers. Suitable viscose rayon fibers are LYOCELL viscose rayon fibers, type 18453, obtained from Courtaulds Fibers, Inc. of North Axis, Alabama. Suitable eucalyptus fibers are eucalyptus grandis, obtained from Aracruz, Brazil. The fibers may be blended together and formed into a web by a variety of methods including wet-laying method, air-laying method, carding, needle punching or other methods. Air-laying method and needle punching are particularly preferable.

The distribution member 33 is also flexible, and the acquisition portion 25 of the distribution member 33 is especially flexible. The flexibility of the distribution member 33 allows the absorbent article 20 to maintain sustained contact with and cover a portion of the surface of the wearer's labia minora preferably in cooperation with the specially designed supporting garment. Further, by the flexibility, the acquisition portion 25 of the distribution member 33 can easily protrude through the storage member opening 31A and the topsheet opening 28A, and then, acquisition portion 25 can extend over the topsheet 28 longitudinally outwardly or laterally outwardly beyond the periphery edge 31E of the storage member opening 31A.

The absorbent article 20 of the present invention has an acquisition portion 25 which is a portion of a distribution member 33 and a periphery portion 27 which is a portion of the topsheet 28. The acquisition portion 25 positions generally at the center of the absorbent article 20 such that the acquisition portion 25 includes at least a portion of the absorbent article 20 along the longitudinal centerline L. Suitable configurations to the top view of the acquisition zone 25 include, but are not limited to, rectangle shape, triangle shape, or polygon shape. Alternatively, the configuration of the top view of the acquisition portion 25 may have oval shape, race-track shape, or circle shape, or any other shapes which is suitable as an acquisition portion to effectively acquire body fluid at the source of the body fluid.

Figure 4:
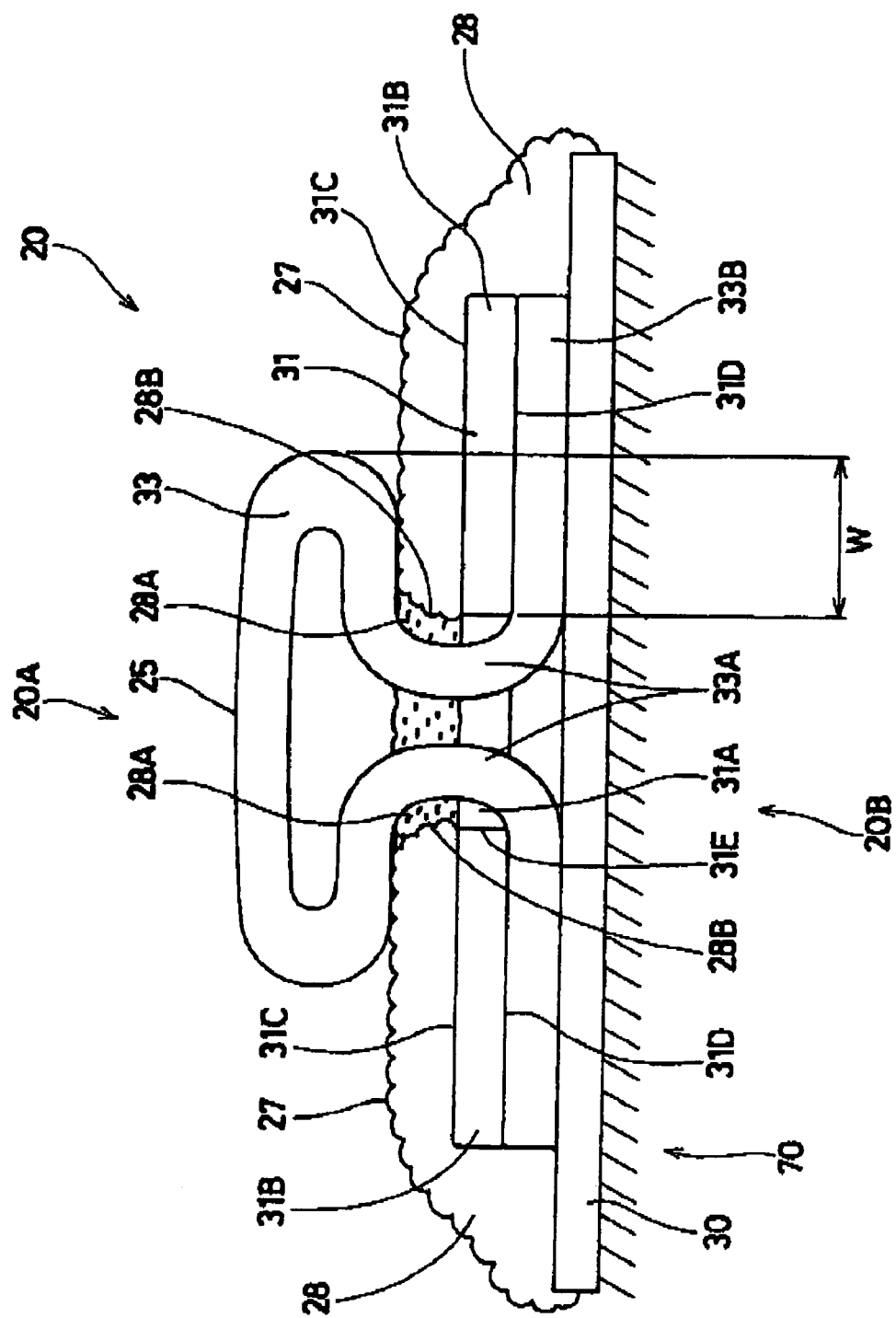
FIG. 4 is a cross-sectional view of the absorbent article shown in FIG. 1, taken along line X—X.

Referring to FIG. 4, the configuration of the transverse cross section of the acquisition portion 25 is substantially "omega-shape". By the configuration "omega-shape" of the transverse cross section of the acquisition portion 25, while the size of each of the openings 28A and 31A is small, the contact area of the acquisition portion 25 to a portion of the surface of the wearer's labia minora can be large, and the area of the storage portion 31B can be large. Therefore, it is possible to provide the absorbent article which has an enhanced absorption capacity for body fluid because it is possible to make the area of the storage portion 31B larger.

The acquisition portion 25 of the distribution member 33 protrudes through the storage member opening 31A and the topsheet opening 28A such that it directly contacts the wearer's body, such as a portion of the surface of the wearer's labia minora. The majority of body fluid can be rapidly acquired by the acquisition portion 25 of the distribution member 33 through the topsheet opening 28A and the storage member opening 31A because of the acquisition performance and intimate body contact of the acquisition portion 25 of the distribution member 33. Because of the storage member opening 31A, the storage portion 31B has less tendency to be exposed to gushes of body fluid. Thus, body fluid is acquired by the acquisition portion 25 of the distribution member and distributed underneath the storage portion 31B. Since body fluid is sometimes discharged in gushes, the acquisition portion 25 should be able to rapidly acquire and transport body fluid from the wearer's body to an element of the absorbent article 20, such as preferably to the absorbent component 32 with a minimum of body fluid flow resistance. The acquisition portion 25 also preferably provides improved rates of body fluid acquisition. The acquisition portion 25 protrudes through the topsheet 28 and directly contacts with the wearer's labia minora, therefore is able to directly and rapidly acquire discharged body fluid without a resistance against body fluid flow. The acquisition portion 26 is also so flexible that the acquisition portion 25 is able to maintain sustained contact with a portion of the surface of the wearer's labia minora. The sustained contact secures the acquisition portion to acquire body fluid without leakage or with minimal leakage of body fluid outside the acquisition portion 25 over a period of use of the absorbent article.

The acquisition portion 25 is preferably placed in a specific positional relationship with respect to the area of typical body fluid deposition of the absorbent article 20 and with respect to a specific portion of the wearer's body where body fluid is discharged. Thus, the acquisition portion 25 is placed in the vicinity of the point of discharge of body fluid so as to be capable of rapidly acquiring a majority of body fluid at their contact zone. It is preferable that the acquisition portion 25 covers at least a portion of the surface of the wearer's labia minora. The acquisition portion 25 preferably covers portions of the interior surfaces of the wearer's labia minora such that the acquisition portion fits interlabially between the interior surfaces of the wearer's labia minora. More preferably, the acquisition portion 25 covers substantially all of the interior surfaces of the wearer's labia minora up to and including contacting and covering the floor of the wearer's vestibule. The acquisition portion 25 may cover portions of the exterior surfaces of the wearer's labia minora. The acquisition portion 25 may cover portions of both the interior surface and the exterior surface of the wearer's labia minora. The acquisition portion 25 may cover a portion of the surface of the wearer's labia majora. The acquisition portion 25 which is able to cover a portion of the wearer's labia majora tolerates a degree of misplacement of the absorbent article with the wearer's body, yet covers the desired portion of the wearer's body, thereby ensuring a majority of, preferably all of, body fluid to be acquired through the acquisition portion 25.

The dimension of the acquisition portion 25 is preferably designed to cover the dimension of the surface of the wearer's labia minora. The acquisition portion 25 may extend into a portion of the surface of the wearer's labia majora. However, it is preferable that the acquisition portion 25 does not extend beyond the wearer's labia majora and does not cover the surface of the wearer's body outside the labia majora.

The overall length of the acquisition portion 25 is preferably chosen to cover at least a portion of the surface of the wearer's labia minora, preferably to cover the entire length of the wearer's labia minora, when the absorbent article is applied to the wearer's body. The width of the acquisition portion 25 is preferably chosen to have a width covering at least a portion of the wearer's labia minora, preferably the surface of the wearer's labia minora in taking the wearer's labia minora depth into account when the acquisition portion 25 of the absorbent article 20 is inserted interlabially between the wearer's labia minora. More preferably, the overall length and/or width of the acquisition portion 25 are chosen to be able to allow some tolerance of absorbent article placement against the wearer's body.

In one embodiment, when the configuration of the top view of the acquisition portion 25 has a rectangular shape as shown in FIG. 2, the acquisition portion 25 may have an overall length of less than or equal to about 120 mm, preferably less than or equal to about 100 mm, more preferably less than or equal to about 80 mm, and of more than or equal to about 30 mm, preferably more than or equal to about 40 mm, more preferably more than or equal to about 50 mm. The acquisition portion 25 may have a width of less than or equal to about 60 mm, preferably less than or equal to about 50 mm, more preferably less than or equal to about 40 mm, and of more than or equal to about 5 mm, preferably more than or equal to about 7 mm, more preferably more than or equal to about 10 mm.

In the preferred embodiment shown in FIG. 4, preferably, the width W may be greater than or equal to 2 mm, more preferably greater than or equal to 5 mm. However, the width W should be less than half of the width T1 shown in FIG. 2.

After the absorbent component 32 acquires body fluid, the absorbent component 32 becomes wet. Typically, the absorbent component 32 having a high ability to acquire body fluid is highly wettable. Although such a wet portion (the acquisition portion 25) of the distribution member 33 protrudes through the topsheet opening 28A and the storage member opening 31A, and contacts at least the portion of the surface of the wearer's labia minora, the wearer does not feel wetness or feels minimal wetness because the portion where the absorbent component 32 contacts is limited. It is believed that the wearer does not feel wetness or is less sensitive to feeling wetness at the surface of the labia minora than at a portion of the surface of the wearer's body outside the wearer's labia minora. Typically, the wearer becomes more sensitive to feeling wetness as it goes outwardly from the surface of the wearer's labia minora toward the surface of the wearer's labia majora, further toward the surface of the wearer's body outside the wearer's labia majora. Therefore, the acquisition portion 25 should have minimal to no extension beyond the labia majora so as to minimize giving wet feeling to the wearer.

It is possible to provide the absorbent article which relatively quickly acquires body fluid discharged from the wearer's body and moves absorbed body fluid into the absorbent article because the acquisition portion 25 protrudes through the storage member opening 31A and the topsheet opening 28A. Further, it is possible to provide the absorbent article which relatively quickly moves absorbed body fluid away from the wearer's body because the acquisition portion 25 and the main portion 33B are connected by the connecting portion 33A with having liquid permeability between the acquisition portion 25 and the main portion 33B, and the acquisition portion 25 is disposed above the main portion 33B. Further, the acquisition portion 25 extends over the topsheet 28 longitudinally outwardly or laterally outwardly beyond the periphery edge 31E of the storage member opening 31A, therefore it is possible to provide the absorbent article which has an enhanced absorption capacity for body fluid because it is possible to make the area of the storage portion 31B larger.

In another embodiment, the absorbent component 32 may have an additional storage member which is disposed underneath the main portion 33B of the distribution member 33. The additional storage member provides additional capacity to the absorbent article 20 and helps to draw body fluid acquired in the distribution member 33 such that the distribution member 33 becomes available for second gush. The additional storage member may have the generally same or similar size and shape with the storage member 31. However, the additional storage member may have different size and shape from the storage member 31. For example, the additional storage member may have an oval shape and may be disposed underneath the main portion 33B of the distribution member 33. When the additional storage member is disposed underneath the main portion 33B of the distribution member 33, the additional storage member may be flexible. Preferably, the entire portion of the additional storage member is flexible. The additional storage member may be formed by any known materials. Preferably, the additional storage member is formed by the materials described above for the storage member 31 of the absorbent component 32.

The backsheet 30 can be any suitable flexible, liquid impermeable material. Preferably, the backsheet 30 is a polyethylene film having a thickness of from about 0.012 mm to about 0.015 mm. Exemplary polyethylene films are manufactured by Clopay Corporation of Cincinnati, Ohio, under the designation P18-0401 and microflex 1401. The backsheet 30 may be embossed and/or matte finished to provide a more clothlike appearance.

Further, the backsheet 30 may permit vapors to escape from the absorbent component 32 (that is, it may be breathable) while still preventing exudates from passing through the backsheet. A suitable breathable backsheet material comprises an adhesively attached laminate of an apertured film having tapered capillaries, such as that described in U.S. Pat. No. 3,929,135 issued to Thompson on Dec. 30, 1975, and a microporous film. A suitable microporous film is supplied by Exxon Chemical USA, and described in Exxon's U.S. Pat. No. 4,777,073. The breathable backsheet is arranged so that the smaller openings of the tapered capillaries face the absorbent component 32. The microporous film is joined to the side of the apertured film having the larger openings to form the garment facing side 20B of the absorbent article. Alternatively, the breathable backsheet material may comprise a vapor permeable monolythic film. The monolythic film is advantageous as they can provide high levels of latent heat transfer while preventing soil-through and also while reducing the stiffness of the absorbent article.

The use of a breathable backsheet in conjunction with the menstrual panty (described in greater detail below), which preferably has a breathable crotch portion, allows the overall breathability of the system of the absorbent article and the menstrual panty to be controlled and set to an optimal level. This eliminates any variances caused by using the absorbent article randomly with commercially available undergarments that have different amounts of vapor permeability and non-permeability.

The topsheet 28, the backsheet 30, and the absorbent component 32 may be assembled in a variety of configurations known in the art (including layered or "sandwich" configurations and wrapped or "tube" configurations). In the preferred embodiments shown in the drawings, the topsheet 28 and the backsheet 30 have length and width dimensions generally larger than those of the absorbent component 32. The topsheet 28 and the backsheet 30 extend beyond the edges of the absorbent component 32 to form portions of the periphery 26. The portions of the topsheet 28 and backsheet 30 that extend beyond the edges of the absorbent component 32 to form the periphery 26, are preferably joined to each other.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

The components of the absorbent article can be described as forming a "unitary structure." The term "unitary structure", as used herein, refers to a construction in which the components are joined together, or integrated together as a unit. The term "unitary structure" includes constructions such as those described above where the topsheet, absorbent core, and backsheet comprise separate components that are joined together. It also covers constructions in which the liquid permeable side and liquid impermeable side of the absorbent articles do not comprise a separate topsheet and/or backsheet. For example, in the latter case, the liquid permeable side, the liquid impermeable side, or both, may comprise a surface of the absorbent component that has the desired characteristics, rather than a separate component.

Figure 5:
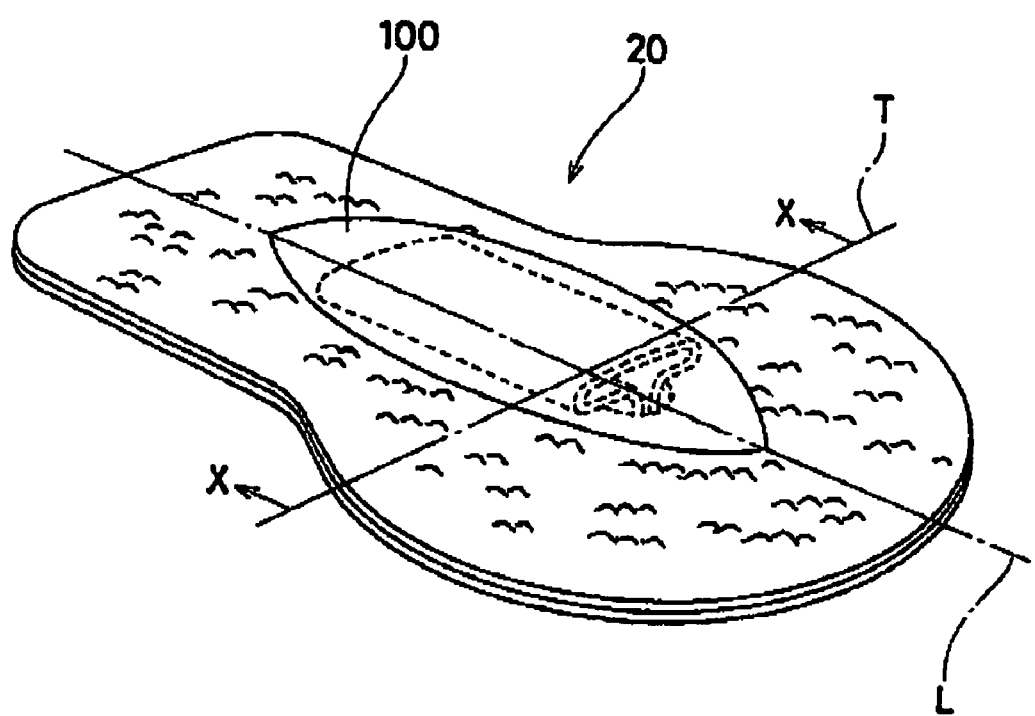
FIG. 5 is a perspective view of an alternative embodiment of the absorbent article having a sub-topsheet.
Figure 5A:
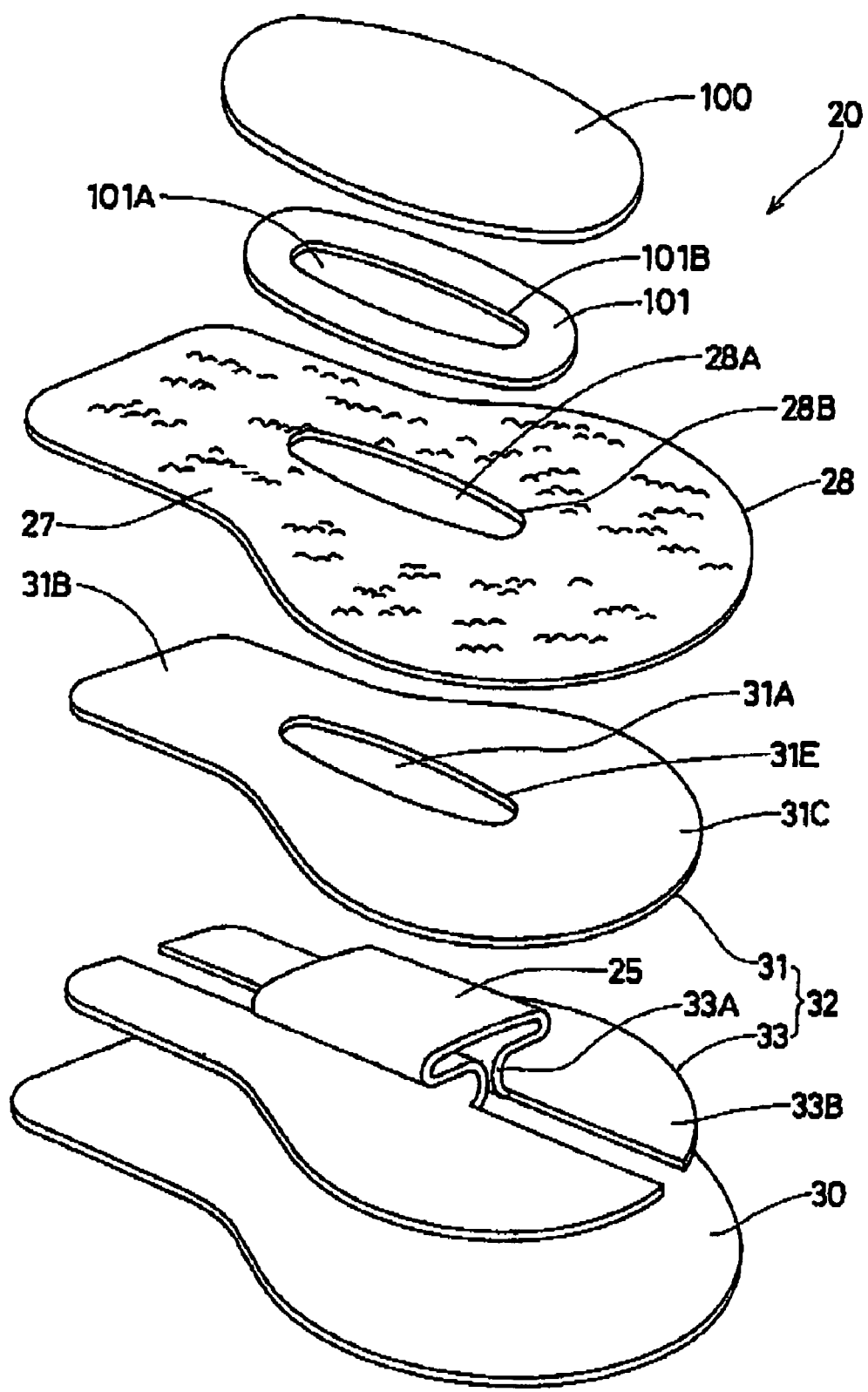
FIG. 5A is an exploded perspective view of the absorbent article shown in FIG. 5.
Figure 5B:
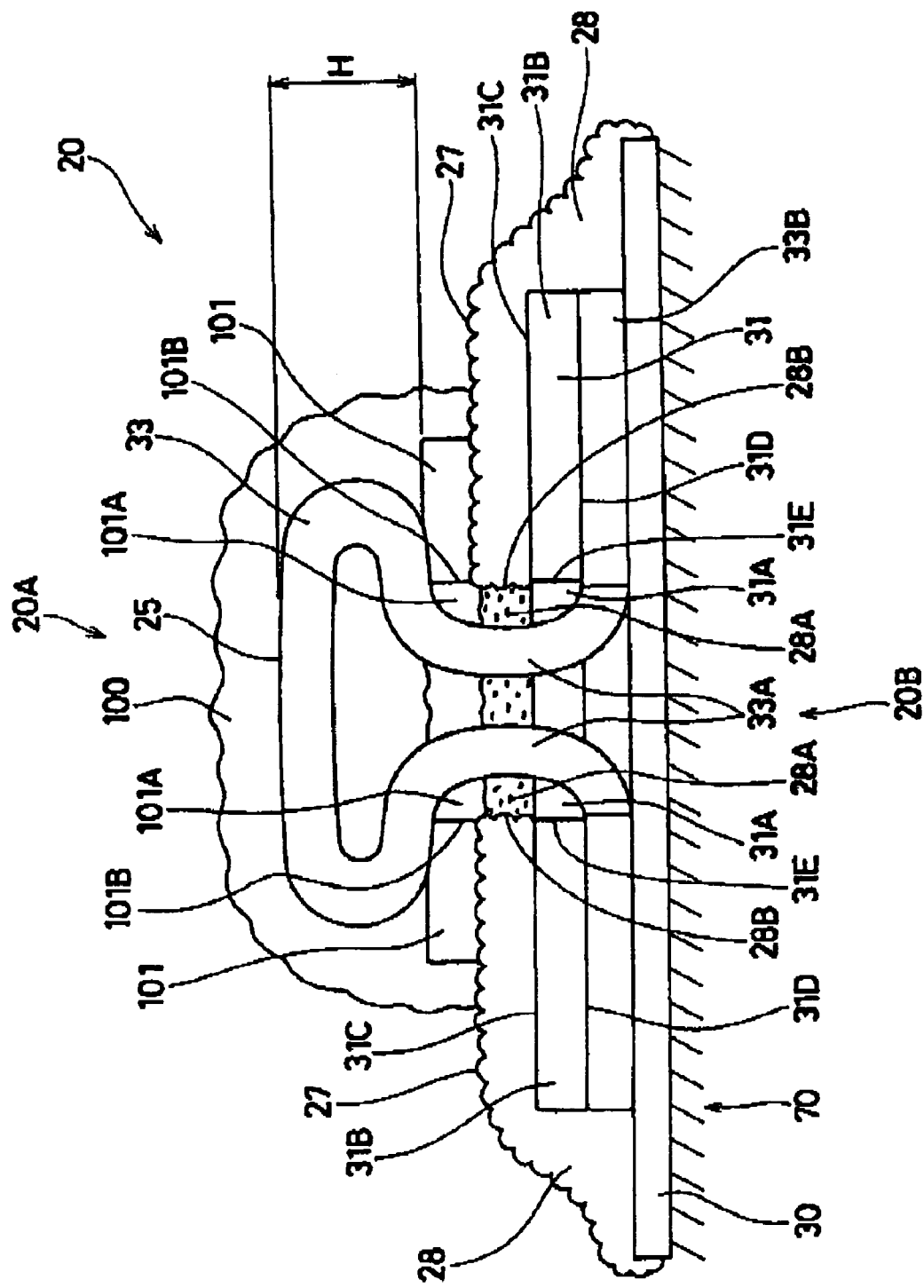
FIG. 5B is a cross-sectional view of the absorbent article shown in FIG. 5, taken along line X—X.

In other embodiment, it is preferable that the absorbent article 20 further comprises a sub-topsheet 100 and a sub-backsheet 101 (refer to FIGS. 5, 5A and 5B). In this embodiment, the sub-topsheet 100 is placed over the acquisition portion 25, and covers the whole of the acquisition portion 25. The sub-backsheet 101 is placed between the acquisition portion 25 and the topsheet 28, and has a sub-backsheet opening 101A. The sub-backsheet opening 101A is surrounded by a sub-backsheet periphery edge 101B. Further, the sub-topsheet 100 and the sub-backsheet 101 may be joined by a regular or irregular patterned layer of adhesive, or any array of separate lines, spirals, or spots of adhesive. Alternatively, they may be joined by any other methods, such as bonding by applying pressure. Accordingly, the acquisition portion 25 of the distribution member 33 protrudes through the storage member opening 31A, the topsheet opening 28A and sub-backsheet opening 101A. Further, the acquisition portion 25 extends over the topsheet 28 and the sub-backsheet 101 at least longitudinally outwardly or laterally outwardly beyond the periphery edge 31E of the storage member opening. Because of having the sub-topsheet 100 and the sub-backsheet 101, it is possible to hold the configuration of the acquisition portion 25. Therefore, for example, it is possible to make the height H of the acquisition portion 25 in FIG. 5B lower. Accordingly, it is possible to make the overall height of the absorbent article 20 lower.

The absorbent article 20 preferably comprises the sub-topsheet 100 and the sub-backsheet 101 as FIGS. 5, 5A and 5B. But the absorbent article 20 may comprise neither the sub-topsheet 100 nor the sub-backsheet 101 as shown in FIGS. 1 to 3.

The garment facing side 20B of the absorbent article 20 may include, and preferably does include a fastener for attaching the absorbent article to the specially designed supporting undergarment. Fasteners comprising adhesives, particularly pressure sensitive adhesives, which have been used to secure absorbent articles, such as sanitary napkins, to the crotch region of conventional panties can be used for this purpose.

Figure 6:
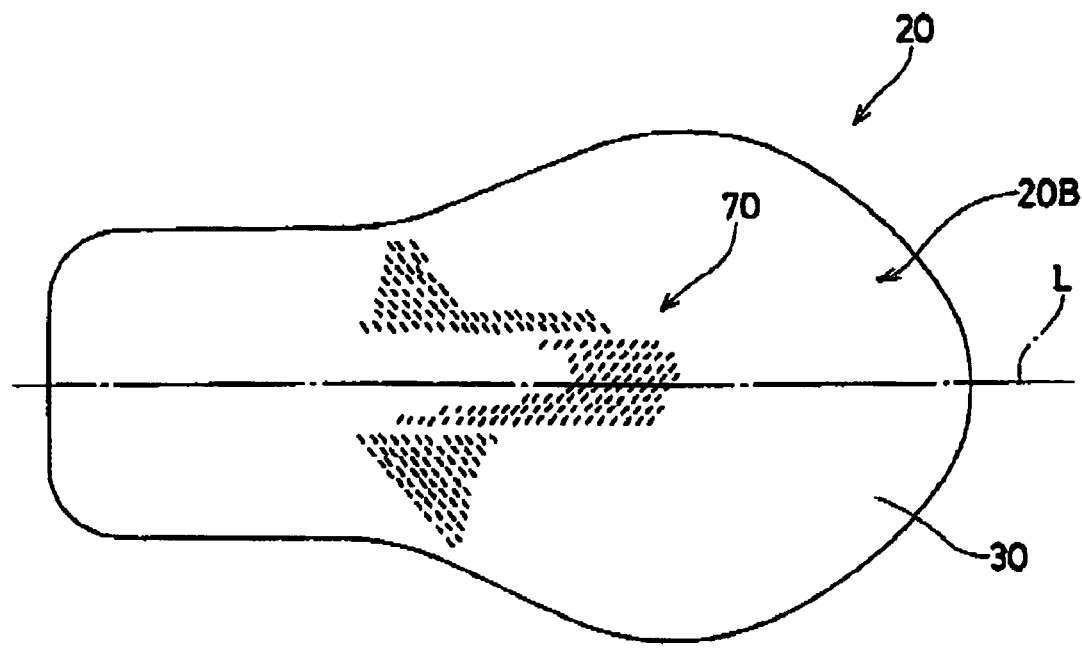
FIG. 6 is a bottom plan view of the absorbent article shown in FIG. 1.
Figure 7:
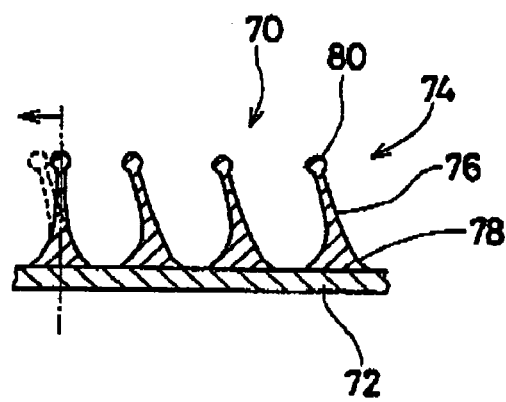
FIG. 7 is an enlarged side view of the mechanical fastening material on the garment-facing side of the absorbent article.

Preferably, however, as shown in FIGS. 4 and 6, the garment-facing surface 20B of the absorbent article 20 comprises a mechanical fastening material 70 that is particularly suitable for engaging knit materials, such as the material from which the specially designed supporting undergarment is preferably made. One type of mechanical fastening material is shown in FIGS. 4, 6, 7. The mechanical fastening material 70 can be located on any suitable portion of the garment facing side 20B. Preferably, as shown in FIG. 6, the mechanical fastening material 70 is located on the entire portion of the garment-facing surface 20B. In other embodiments, the mechanical fastening material 70 could cover all, or any other suitable portion of the garment facing side 20B of the absorbent article.

The mechanical fastening material 70 shown in FIG. 7 comprises a substrate or surface 72 with an array of prongs in the form of a plurality of small filamentous (or hair-like) projections 74 extending therefrom. The hair-like projections 74 may be of any suitable shape. FIG. 7 shows one preferred shape of the projections 74 in greater detail. The hair-like projections 74 may, but need not, have a hook shape like conventional VELCRO hook fastening material. In the embodiment shown in FIG. 7, the hair-like projections 74 preferably do not have a hook shape. The hair-like projections 74 preferably have a straight shank 76 that tapers so that it generally decreases in diameter from the base 78 of the shank 76 toward the distal end of the shank. More specifically, the shank 76 decreases in diameter from the base 78 of the shank 76 toward the distal end of the shank until about the mid-point of the shank. The diameter of the shank 76 remains constant from about the mid-point of the shank to the distal end of the shank 76. The distal end of the shank 76 preferably has a small spherical engaging means 80 thereon. The hair-like projections 74 in the preferred embodiment shown in the drawings preferably extend at a slight angle from an orientation that is perpendicular (that is, at an angle of about 90 degrees) from substrate. Preferably, the hair-like projections 74 are oriented at an angle that is about 10° less than a perpendicular orientation relative to the substrate.

The mechanical fastening material 70 can be distributed in any suitable pattern across the garment facing side 20B. In a particularly preferred embodiment, as shown in FIG. 6, the mechanical fastening material 70 is distributed in several zones (e.g., three zones, each about 2 cm (about 0.75 inches) wide) in which the orientation of the hair-like projections differs between adjacent zones. More specifically, in the embodiment shown in FIG. 6, the hair-like projections in a central zone that runs along the longitudinal centerline L are oriented at an angle that is about 10° less than a perpendicular orientation relative to the substrate which is oriented toward one end of the absorbent article. The hair-like projections in the adjacent longitudinal side zones form a similar angle relative to the substrate, but they are oriented toward the opposite end edge of the absorbent article 20. The orientation of the hair-like projections in these different zones is shown by arrows in FIG. 6.

Figure 8:
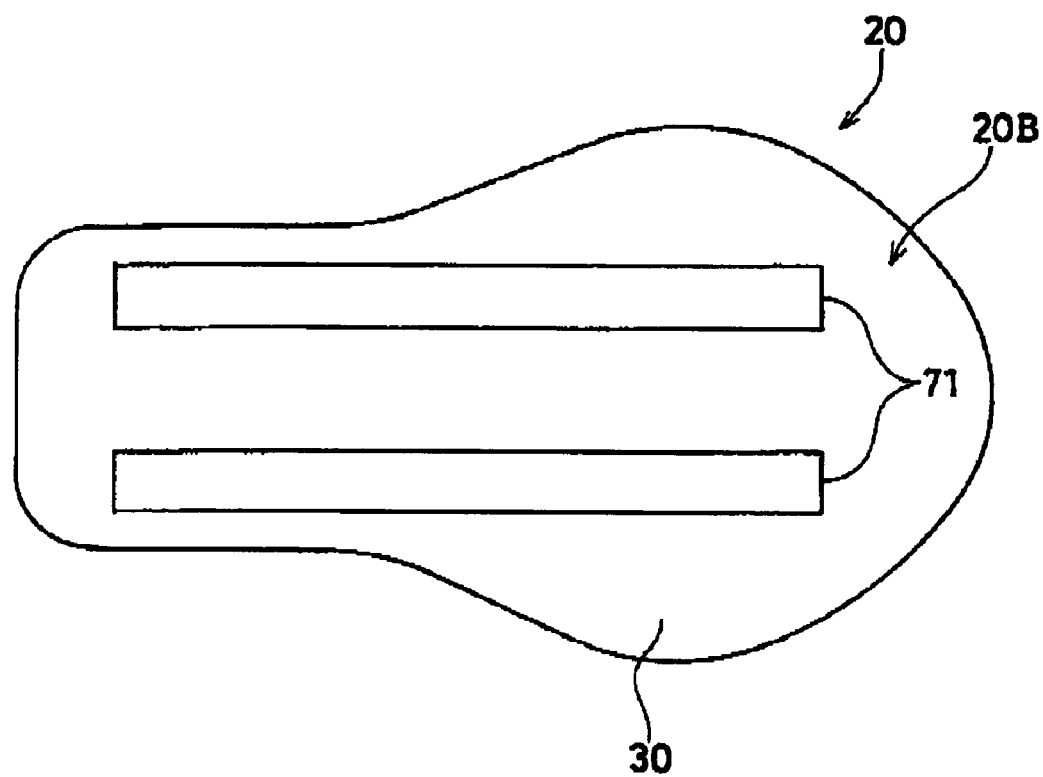
FIG. 8 is a bottom plan view of an alternative embodiment of the absorbent article.

In other embodiments, the mechanical fastening material 70 can be distributed in a pattern that matches the pattern of one or more pre-selected portions of the specially designed supporting garment. For example, the mechanical fastening material 70 can be arranged in a pattern that corresponds to and aligns with the longitudinal stretch control member 52 and/or the angled stretch control members 54 of the menstrual undergarment 38 shown in FIGS. 12 and 13. (The menstrual undergarment is described in greater detail below.) For instance, portions of the mechanical fastening material 70 at each end edges 24 of the absorbent article 20 can be arranged in a chevron pattern to correspond to the angled stretch control members 54 of the menstrual undergarment. In a variation of this embodiment, the mechanical fastening material 70 and/or the other portions of the supporting garment could be designed so that the mechanical fastening material 70 will not engage other than with a particular portion of the supporting garment, such as the longitudinal or angled stretch control members. The alignment of the mechanical fastening material 70 with these portions of the supporting garment can be used as a placement aid to ensure that the absorbent article 20 is positioned properly in the supporting garment. The pattern of mechanical fastening material 70 can also be used to assist the absorbent article 20 in fitting closely against the wearer's body in certain areas. The mechanical fastening material 70 may be disposed in a configuration of two strips 71 as shown in FIG. 8.

The mechanical fastening material 70 shown in FIG. 7 provides the garment facing side 20B of the absorbent article 20 with a fastener that is capable of easily adhering to knit material, and has a sufficiently high holding force even if the supporting garment stretches and contracts. The mechanical fastening material 70 described herein is particularly preferred for use with the specially designed knit supporting undergarment since it will not become detached when the supporting garment stretches and contracts during application of the absorbent article to the undergarment, as will some pressure sensitive adhesives. These and other features are disclosed in PCT Application No. US 98/23861 entitled "Highly Efficient Absorbent Article For Use With Menstrual Pant" filed in the name of Carstens, et al. on Nov. 9, 1998.

In another embodiment, the mechanical fastening material 70 can comprise a material having a "T"-shaped or mushroom-shaped appearance when viewed from the side. One particularly preferred "T"-shaped mechanical fastening material for use on the absorbent article of the present invention is a material known as TP200 available from 3M Personal Care and Related Products Division of Menomonie, Wis.

In addition to the mechanical fastening material described above, and pressure sensitive adhesives, the garment facing side 20B of the absorbent article 20 may employ other alternative types of fasteners. In one non-limiting example, the absorbent article 20 can be provided with a cohesive material that adheres to a cohesive material on the inside of the crotch portion of the supporting undergarment. As used herein, a "cohesive material" is one which preferentially adheres to itself and not to other materials. Such a material can be used as a placement aid to ensure that the absorbent article 20 is positioned properly in the supporting garment.

Figure 12:
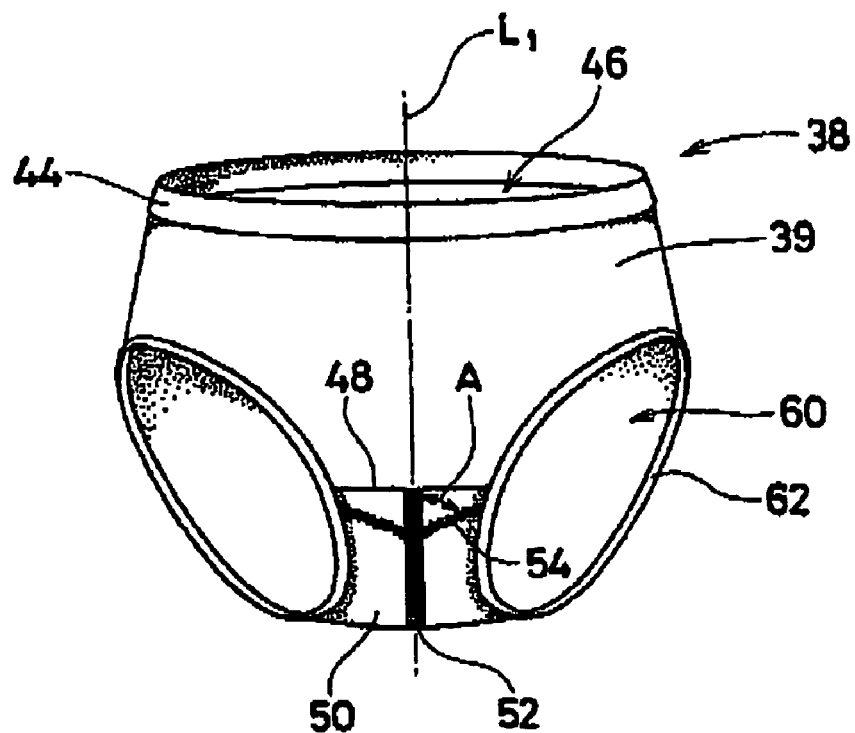
FIG. 12 is a front view of a preferred embodiment of a menstrual undergarment for use with the absorbent article of the present invention.
Figure 13:
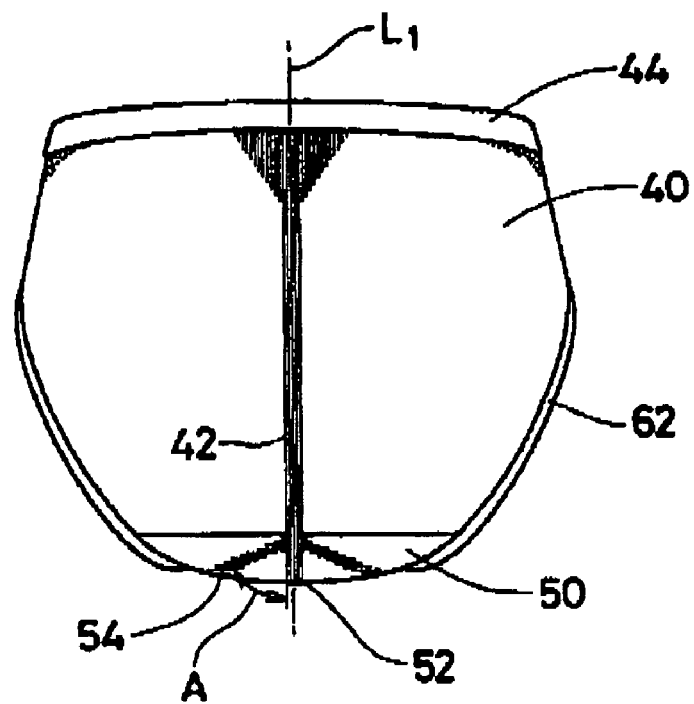
FIG. 13 is a rear view of a preferred embodiment of a menstrual undergarment for use with the absorbent article of the present invention.

FIGS. 12 and 13 show front and rear views of a supporting garment in the form of a menstrual undergarment 38 that is preferred for use with the present invention. As is shown in FIGS. 12 and 13, the menstrual undergarment 38 comprises a front portion 39 which may be in the form of a front panel, a rear portion 40 which may be in the form of a rear panel, a crotch region or portion 50 which may be in the form of a crotch panel, a pair of leg openings 60 which may be elasticized, and an elasticized waistband 44. The menstrual undergarment 38 is also provided with a waist opening 46 allowing entry into the menstrual undergarment 38. The menstrual undergarment 38 further comprises an extensible lifting member such as lifting strip 42 disposed along the longitudinal centerline $L_1$ in the rear portion 40, a longitudinal stretch control member 52 disposed along the longitudinal centerline in the crotch portion 50, and a plurality of angled stretch control members 54 disposed at an angle A with respect to the longitudinal stretch control member 52 and extending therefrom to the leg elastics 62. It should be noted that any seam or gusset 48 at the front end of the crotch portion 50 is preferably situated so that it lies under or behind (that is, rearward of) the pubic bone so that the pubic bone does not interfere with the fit of the menstrual undergarment. It should also be understood that any or all of the features of the menstrual undergarment 38 described herein may be knit into the menstrual undergarment, and need not comprise sewn together portions of the menstrual undergarment.

The absorbent article 20 is utilized by placing the absorbent article 20 in the crotch portion of the menstrual undergarment 38. The absorbent article 20 is placed in the crotch portion of the menstrual undergarment with one end extending toward the front section of the menstrual undergarment and the other end towards the back section of the menstrual undergarment. The backsheet 30 is placed in contact with the inner surface of the center of the crotch portion 50 of the menstrual undergarment. The hair-like projections 74 of the mechanical fastening material 70 on the garment facing side 20B of the absorbent article 20 engage with the knit material from which the crotch portion 50 of the menstrual undergarment 38 is made. The wearer then pulls on the menstrual undergarment 38. The absorbent article 20 may be first applied to the wearer's body, then the wearer may pull on the menstrual undergarment 38. The menstrual undergarment 38 helps the acquisition portion 25 of the distribution member 33 of the absorbent article 20 maintain sustained fit and contact with the wearer's body. The menstrual undergarment 38 also helps the flexible absorbent article 20 conform to the body shape and maintain sustained fit with the wearer's body.

Figure 9:
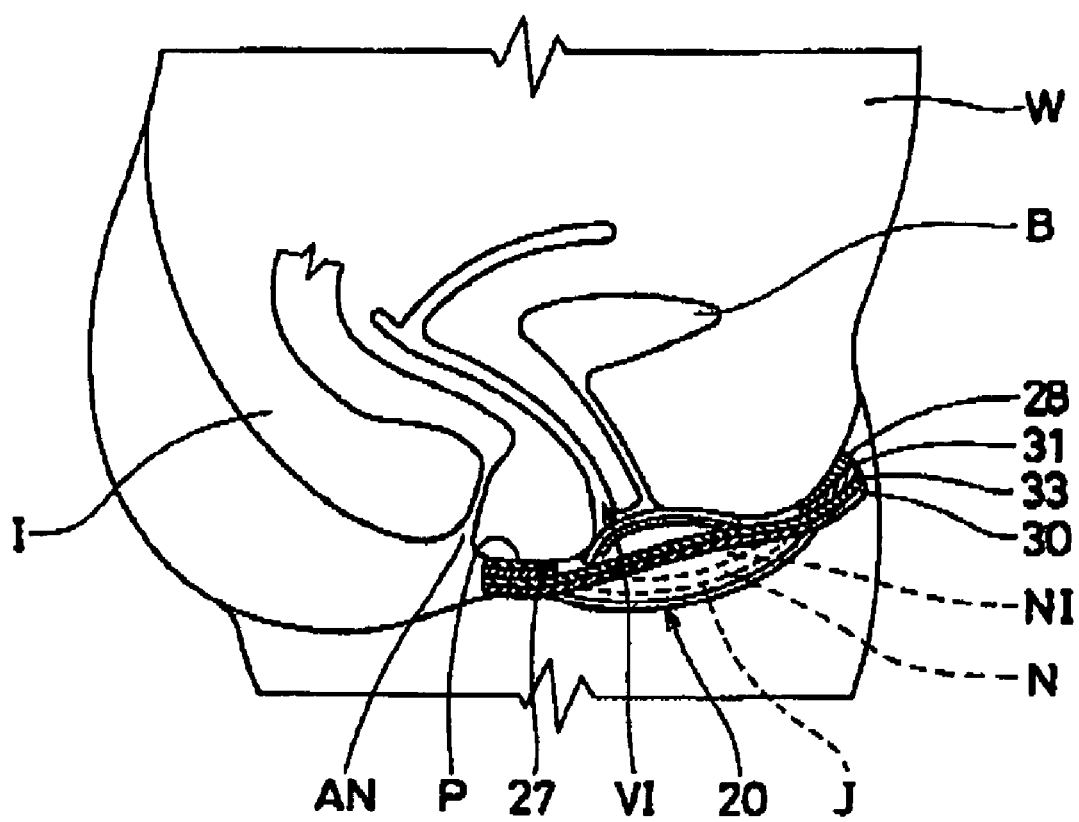
FIG. 9 is a cross-sectional sagittal view of a human female wearer showing the absorbent article of the present invention in one disposition.
Figure 10:
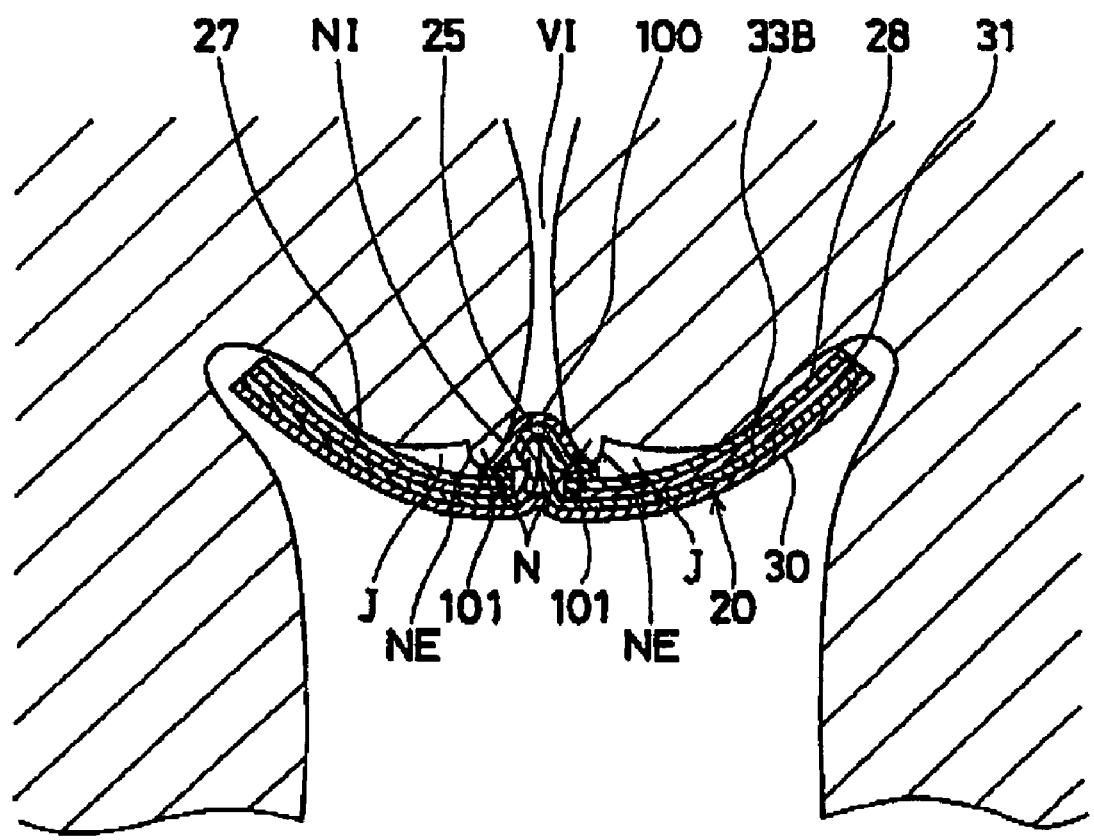
FIG. 10 is a transverse cross-sectional view of a human female wearer showing the absorbent article of the present invention in the disposition shown in FIG. 9.
Figure 11:
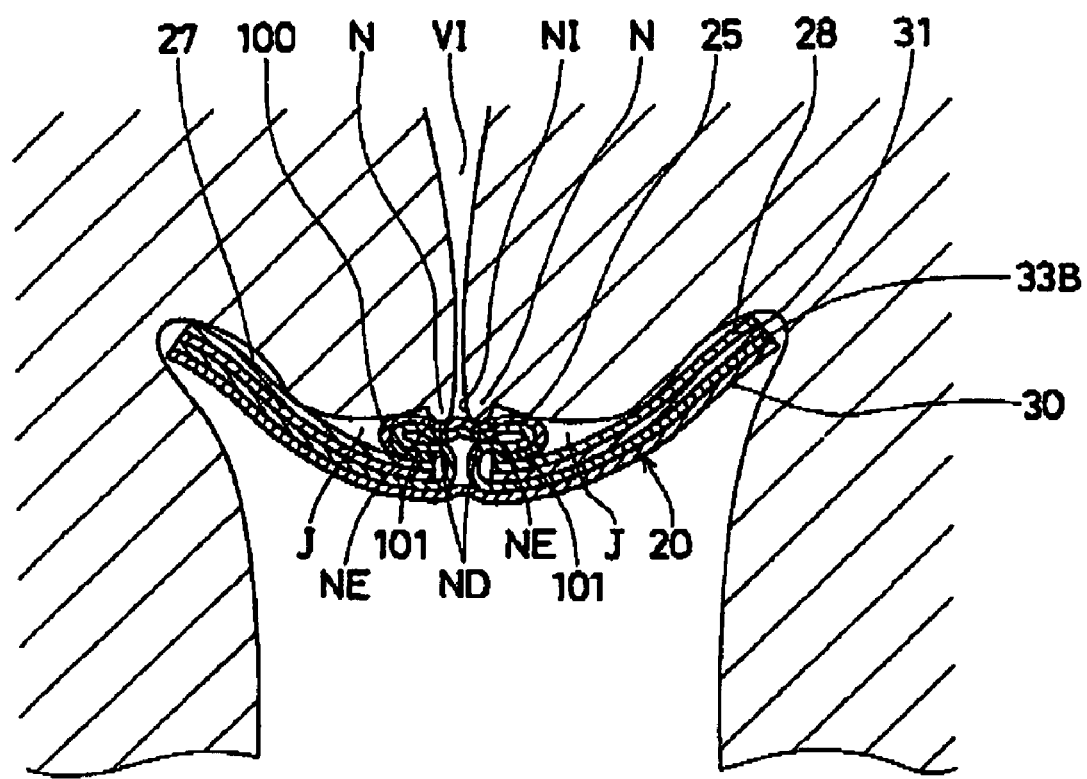
FIG. 11 is a transverse cross-sectional view of a human female wearer showing the absorbent article of the present invention in alternative disposition.

FIGS. 9–11 show a preferred embodiment of the absorbent article 20 of the present invention worn against the body of a wearer W. The urogenital members shown in FIG. 9 include the bladder B, the vagina V, the urethra U, the large intestine I, the anus AN, the vaginal introitus VI, the perineum P, the labia minora N including the interior surface of the labia minora NI and the exterior surface of the labia minora NE (not shown in FIG. 9), and the labia majora J. The interior surface NI of the labia minora N continuously extending from the vaginal introitus VI. Therefore, body fluid such as menses is known to be eventually discharged through the space between the interior surfaces NI of the labia minora N. Contact of a portion of the absorbent article with the interior surfaces NI provides an opportunity to intercept body fluid flowing through the space between the interior surfaces NI and directly acquires body fluid from there before body fluid reaches the surface of the wearer's body outside the labia minora. Contact of a portion of the absorbent article with the exterior surfaces NE also provides an opportunity to acquire body fluid discharged through the space between the interior surfaces NI of the labia minora N before body fluid reaches the surface of the wearer's body outside the labia minora. FIGS. 9–11 show one example of the relationship of these anatomical features of the wearer W to the absorbent article 20 when the absorbent article 20 is properly worn (In FIGS. 9–11, the undergarment 38 is eliminated).

FIGS. 9 and 10 show one non-limiting example of the manner in which the absorbent article 20 may fit adjacent to the wearer's body. In the embodiment shown in FIGS. 9 and 10, the acquisition portion 25 of the distribution member 33 of the absorbent article 20 resides in the space between the portions of the interior surfaces NI of the wearer's labia minora N such that the acquisition portion 25 covers the portions of the interior surfaces NI of the wearer's labia minora N. The acquisition portion 25 of the distribution member 33 protruded through the storage member opening 31A and the topsheet opening 28A directly contacts the portions of the interior surfaces NI of the wearer's labia minora N and is able to directly acquire body fluid into the distribution member 33. The acquisition portion 25 of the distribution member 33 works as if "sealing" the space between the interior surfaces NI of the labia minora N. This reduces the opportunity of body fluid reaching the surface of the wearer's body outside the labia minora N. Although the acquisition portion 25 of the distribution member 33 protruded through the storage member opening 31A and the topsheet opening 28A becomes wet, the wearer does not feel wetness or feels minimal wetness because the wet distribution member primarily contacts portions of the interior surfaces of the wearer's labia minora N. The acquisition portion 25 maintains sustained contact with portions of the interior surfaces of the wearer's labia minora. Preferably, the absorbent article 20 maintains sustained contact with the portions of the surfaces of the wearer's body. In FIGS. 9–11, there are some gaps between the absorbent article 20 and the portions of the wearer's body. This is to more clearly show the shape of each absorbent article 20 and portions of the wearer's body. However, in the actual wearing situation, the absorbent article 20 may fit and contacts more closely to the portions of the wearer's body.

As shown in FIG. 9, the periphery portion 27 of the topsheet 28 is disposed to contact and cover the surface at the wearer's mom's pubis and the wearer's perineum P. The absorbent article may cover the wearer's clitoris, but preferably does not extend substantially forward beyond the wearer's mons pubis. The absorbent article 20 may be spaced slightly away from the clitoris, or it may fit closely against the clitoris, as it does relative to the other regions of the wearer's body. The absorbent article 20 preferably does not extend rearward to contact the wearer's anus to avoid sensitive nerve endings therein. When the absorbent article 20 is of this preferred size, it provides a more comfortable, and less noticeable absorbent article since it occludes less of the crotch region of the wearer's body and allows air to circulate around the same. As shown in FIG. 10, the periphery portion 27 of the topsheet 28 is disposed to contact the portion of the surface of the wearer's labia majora J and the surface of the wearer's skin outside the wearer's labia majora J. Body fluid is not directly deposited on the periphery portion 27 of the topsheet 28. Therefore, the periphery portion 27 of the topsheet 28 remains relatively visually clean and relatively dry.

FIG. 11 shows another example of the manner in which the absorbent article 20 may fit adjacent to the wearer's body. In this example, although the acquisition portion 25 of the distribution member 33 does not reside in the space between the portions of the interior surfaces NI of the labia minora N to the extent shown in FIG. 10, the acquisition portion 25 of the distribution member 33 covers the distal portion ND of the wearer's labia minora N and portions of the exterior surfaces NE of the wearer's labia minora N. In this example, the acquisition portion 25 of the distribution member 33 directly contacts the portions of the exterior surfaces NE of the wearer's labia minora N. The distribution member works as if sealing the labia minora by encompassing the portions of the exterior surfaces NE of the wearer's labia minora N. The acquisition portion 25 of the distribution member 33 protruded through the storage member opening 31A and the topsheet opening 28A directly acquires a majority of body fluid flowing through the space between the interior surface NI of the wearer's labia minora N. This prevents body fluid from flowing beyond the exterior surface NE of the wearer's labia minora N. In this embodiment, the periphery portion 27 of the topsheet 28 is disposed to contact the portion of the surface of the wearer's labia majora J and the surface of the wearer's skin outside the wearer's labia majora J.

The absorbent article of the present invention can be provided with still other features. For example, the absorbent article can be provided with an optional pair of flaps that are joined to and extend laterally outward from the longitudinal side edges of the absorbent article. In this case, the absorbent article without the flaps can be considered to comprise the main body portion of the overall absorbent article which has the optional flaps. The flaps preferably extend laterally outward from at least a central region along the length of the main body portion. However, since the main body portion may be relatively small in size, it is possible that the flaps may extend outward along the entire length of the main body portion. In other embodiments, the flaps may even be longer than the main body portion.

If optional flaps are provided, they can be joined to the main body portion of the absorbent article in any suitable manner. The flaps can be integral with the main body portion (that is, the flaps can comprise integral extensions of the topsheet and backsheet). In other embodiments, the flaps can comprise separate components that are joined to the main body portion of the absorbent article.

The flaps can be in any suitable configuration. Suitable flaps are described in Reexamined U.S. Pat. No. B1 4,589,876 entitled "Sanitary Napkin", issued to Van Tilburg, Certificate of Reexamination issued Apr. 27, 1993; U.S. Pat. No. 4,687,478 entitled "Shaped Sanitary Napkin With Flaps", which issued to Van Tilburg on Aug. 18, 1987; U.S. Pat. No. 5,389,094 entitled "Absorbent Article Having Flaps and Zones of Differential Extensibility" issued to Lavash, et al. on Feb. 14, 1995; U.S. Pat. No. 5,558,663 entitled "Absorbent Article Having Undergarment Covering Components With Zones of Extensibility" issued to Weinberger, et al. on Sep. 24, 1996 and U.S. Pat. No. 5,584,829 entitled "Absorbent Articles Having Panty Covering Components That Naturally Wrap the Sides of Panties", issued to Lavash, et al. on Dec. 17, 1996 (which describe alternatives to flaps that are applied by a wearer); PCT Publication No. WO 97/12576 entitled "Absorbent Article Having Flaps With a Deformed Hinge and Zones of Extensibility", published Apr. 10, 1997; and in International Patent Application Serial No. PCT US 96/15957 entitled "Absorbent Article Having Flaps With Step Configuration and Zones of Extensibility" filed on Oct. 3, 1996, in the name of Lash, et al.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

It should also be understood that all of the limits and ranges specified herein include all narrower ranges, limits, and amounts that are within the specified limits and ranges and that such narrower ranges and limits may be claimed even though those limits and ranges are not separately listed.

While particular embodiments of the present invention have been illustrated and described, it would be obvious to those skilled in the art that various other changes and modifications can be made without departing from the spirit and scope of the invention.

The invention claimed is:

1. An absorbent article having a longitudinal centerline and a lateral centerline, the absorbent article comprising a topsheet, a backsheet, and an absorbent component, wherein
   the topsheet has a topsheet opening,
   the absorbent component comprises a storage member and a distribution member,
   the storage member has a storage member opening surrounded by a periphery edge,
   the distribution member comprises an acquisition portion and a main portion wherein,
      the main portion extends underneath the storage member,
      the acquisition portion protrudes through the topsheet opening and the storage member opening, and the acquisition portion extends over the topsheet longitudinally outwardly or laterally outwardly beyond the periphery edge of the storage member opening.

2. The absorbent article of claim 1 wherein the acquisition portion covers a portion of the surface of the wearer's labia minora when the absorbent article is applied on the wearer's body.

3. The absorbent article of claim 2 wherein the acquisition portion extends over the topsheet longitudinally outwardly and laterally outwardly beyond the periphery edge of the storage opening.

4. The absorbent article of claim 3 wherein the acquisition portion has a lateral width of between 5 mm and 60 mm.

5. The absorbent article of claim 3 wherein the acquisition portion has a longitudinal length of between 30 mm and 120 mm.

6. The absorbent article of claim 1 wherein the absorbent component has an additional storage member disposed underneath the main portion of the distribution member.

7. The absorbent article of claim 1 wherein the acquisition portion and the main portion are formed by a single material.

8. The absorbent article of claim 1 wherein the absorbent article has a sub-topsheet which covers the acquisition portion.

9. The absorbent article of claim 8 wherein the absorbent article has a sub-backsheet disposed between the acquisition portion and the topsheet, and the sub-backsheet has a sub-backsheet opening.

* * * * *

UNITED STATES PATENT AND TRADEMARK OFFICE
CERTIFICATE OF CORRECTION

PATENT NO.        : 7,122,023 B1                                        Page 1 of 1
APPLICATION NO.   : 10/168892
DATED             : October 17, 2006
INVENTOR(S)       : Hinoki It is certified that error appears in the above-identified patent and that said Letters Patent is hereby corrected as shown below:

Column 9, line 42, "expected" should read --exposed--.

Signed and Sealed this

Third Day of July, 2007

JON W. DUDAS
*Director of the United States Patent and Trademark Office*